United States Patent
Amit et al.

(10) Patent No.: US 10,590,467 B2
(45) Date of Patent: Mar. 17, 2020

(54) METHODS AND KITS FOR ANALYZING DNA BINDING MOIETIES ATTACHED TO DNA

(71) Applicant: Yeda Research and Development Co. Ltd., Rehovot (IL)

(72) Inventors: Ido Amit, Rehovot (IL); David Lara-Astiaso, Rehovot (IL); Meital Gury, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 354 days.

(21) Appl. No.: 15/303,741

(22) PCT Filed: Apr. 16, 2015

(86) PCT No.: PCT/IL2015/050409
§ 371 (c)(1),
(2) Date: Oct. 13, 2016

(87) PCT Pub. No.: WO2015/159295
PCT Pub. Date: Oct. 22, 2015

(65) Prior Publication Data
US 2017/0037453 A1 Feb. 9, 2017

Related U.S. Application Data

(60) Provisional application No. 61/980,630, filed on Apr. 17, 2014.

(51) Int. Cl.
*C12Q 1/68* (2018.01)
*C07H 21/00* (2006.01)
*C12Q 1/6816* (2018.01)
*G01N 33/53* (2006.01)

(52) U.S. Cl.
CPC ....... *C12Q 1/6816* (2013.01); *G01N 33/5308* (2013.01); *G01N 2440/00* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 5,004,806 A | * | 4/1991 | Kung | C07K 1/34 530/414 |
| 2007/0141583 A1 | * | 6/2007 | Li | C12Q 1/6806 435/6.12 |
| 2014/0024052 A1 | | 1/2014 | Dapprich et al. | |
| 2015/0057163 A1 | * | 2/2015 | Rotem | C12Q 1/6869 506/2 |
| 2019/0203270 A1 | | 7/2019 | Amit et al. | |

FOREIGN PATENT DOCUMENTS

| WO | WO 02/14550 | 2/2002 |
|---|---|---|
| WO | WO 2011/096926 | 8/2011 |
| WO | WO 2012/047726 | 4/2012 |
| WO | WO 2012/050963 | 4/2012 |
| WO | WO 2013/134261 | 9/2013 |
| WO | WO 2015/159295 | 10/2015 |
| WO | WO 2018/020489 | 2/2018 |

OTHER PUBLICATIONS

Asli et al., Genome-wide chromatin maps derived from limited numbers of hematopoietic progenitors. Nature Methodds 7(8):615 (Year: 2010).*
Attema et al., PNAS 104 (30):12371 (Year: 2007).*
Dahl et al., A rapid micro ChIP assay (uChIP). Nature Protocols 3 (6): 1032 (Year: 2008).*
LeFrancois et al., Efficient yeast ChIP-Seq using multiplex short-read DNA sequencing. BMC Genomics 10:37 18 pages (Year: 2009).*
Luger et al., Crystal structure of the nucleosome core particle at 2.8 A resolution. Nature 389:251 (Year: 1997).*
O'Neill et al., Epigenetic characterization of the early embryo with a chromatin immunoprecipitation protocol applicable to small cell populations. Nature Genetics 38 (7):835 (Year: 200).*
Park PJ., ChIP-seq: advantages and challenges of a maturing technology. Nature Reviews Genetics 10:669 (Year: 2009).*
Rotem et al., Single-cell ChIP-seq reveals cell subpopulations defined by chromatin state. Nature Biotechnology 33(11):1165 (Year: 2015).*
Schmidt et al., ChIP-seq: Using high-throughput sequencing to discover protein-DNA interactions. Methods 48:240-248 (Year: 2009).*
Wu et al.,Automated microfluidic chromatin immunoprecipitation from 2,000 cells. Lab on a Chip 9:1365-1370 (Year: 2009).*
Adli et al., Genome-wide chromatin maps derived from limited numbers of hematopoietic progenitors. Nature Methodds 7(8) : 615 (Year: 2010).*
Communication Pursuant to Article 94(3) EPC dated Nov. 15, 2017 From the European Patent Office Re. Application No. 15723307.3. (5 Pages).

(Continued)

Primary Examiner — Ethan C Whisenant

(57) ABSTRACT

A method of analyzing DNA which, in a cell, is bound to a DNA binding moiety, the method comprising:
(a) obtaining at least two samples of complexes of DNA bound to a DNA binding moiety;
(b) isolating the complexes on a solid support;
(c) labeling the DNA of the complexes, wherein the labeling distinguishes between the complexes of the first of the at least two samples and the complexes of the second of the at least two samples;
(d) pooling the at least two samples of complexes; and
(e) isolating the complexes using an agent which specifically binds to the DNA binding moiety; and
(f) analyzing the DNA of the complexes.

14 Claims, 9 Drawing Sheets
(9 of 9 Drawing Sheet(s) Filed in Color)
Specification includes a Sequence Listing.

(56) References Cited

OTHER PUBLICATIONS

International Search Report and the Written Opinion dated Mar. 2, 2017 From the International Searching Authority Re. Application No. PCT/IL2016/050808. (12 Pages).

Communication Pursuant to Article 94(3) EPC dated Apr. 13, 2018 From the European Patent Office Re. Application No. 15723307.3. (6 Pages).

Acevedo et al. "Genome-Scale ChIP-Chip Analysis Using 10,000 Human Cells", BioTechniques, XP002604156, 43(6): 791-797, Dec. 2007.

Dahl et al. "MuChIP—A Rapid Micro Chromatin Immunoprecipitation Assay for Small Cell Samples and Biopsies", Nucleic Acids Research, XP055465549, 36(3): e15-1-e15-8, Published Online Jan. 17, 2008.

Dahl et al. "Q2ChIP, A Quick and Quantitative Chromatin Immunoprecipitation Assay, Unravels Epigenetic Dynamics of Developmentally Regulated Genes in Human Carcinoma Cells", Stem Cells, XP002604155, 25(4): 1037-1046, Published Online Feb. 1, 2007.

Communication Relating to the Results of the Partial International Search dated Jul. 22, 2015 From the International Searching Authority Re. Application No. PCT/IL2015/050409.

International Search Report and the Written Opinion dated Oct. 1, 2015 From the International Searching Authority Re. Application No. PCT/IL2015/050409.

Blecher-Gonen et al. "High-Throughput Chromatin Immunoprecipitation for Genome-Wide Mapping of In Vivo Protein-DNA Interactions and Epigenomic States", Nature Protocols, XP055200053, 8(3): 539-554, Published Online Feb. 23, 2013. Fig.1.

Lara-Astiaso et al. "Chromatin State Dynamics During Blood Formation", Science, XP055200052, 345(6199): 943-949, Published Online Aug. 7, 2014.

Sadeh et al. "Elucidating Combinatorial Chromatin States by Co-ImmunoPrecipitation (Comb-ChIP)", BioRxiv Preprint, 23 P., Jun. 27, 2016.

International Preliminary Report on Patentability dated Feb. 7, 2019 From the International Bureau of WIPO Re. Application No. PCT/IL2016/050808. (8 Pages).

\* cited by examiner

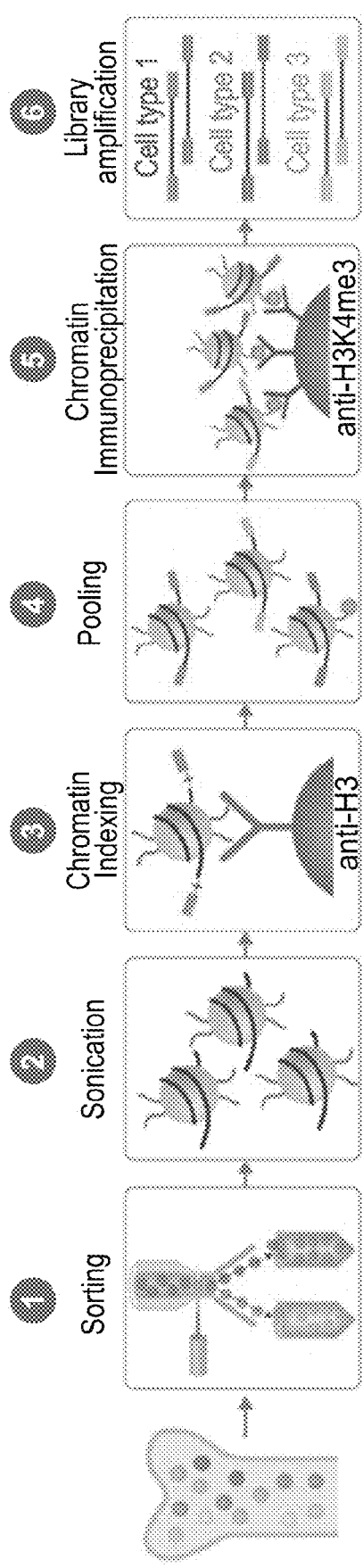
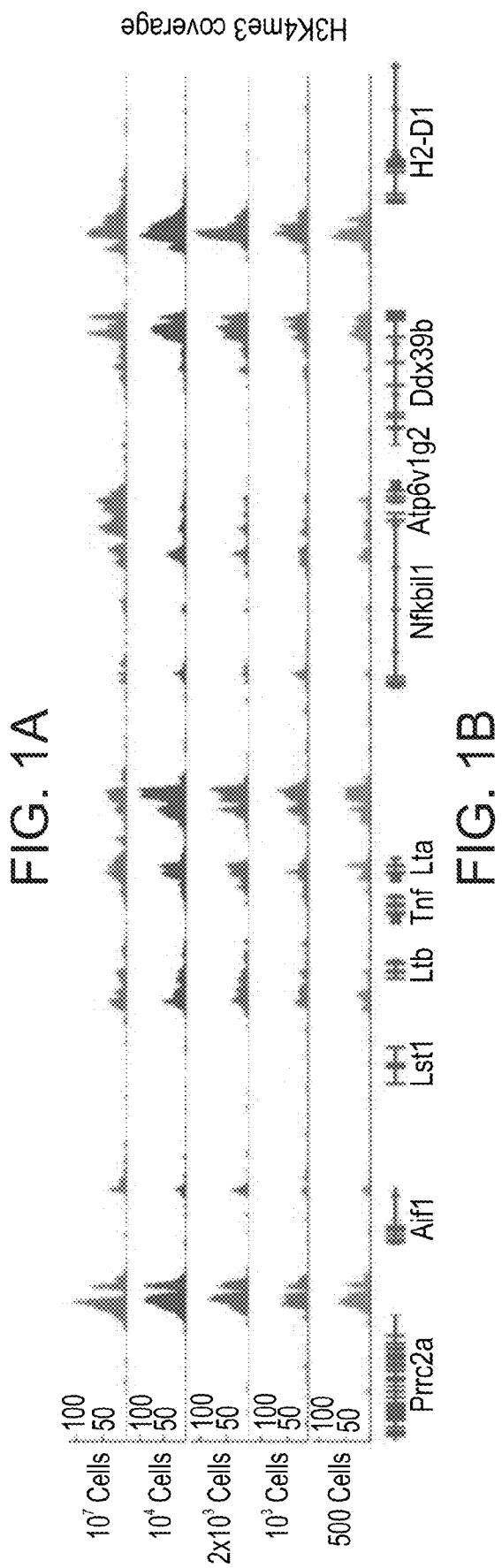
FIG. 1A
FIG. 1B

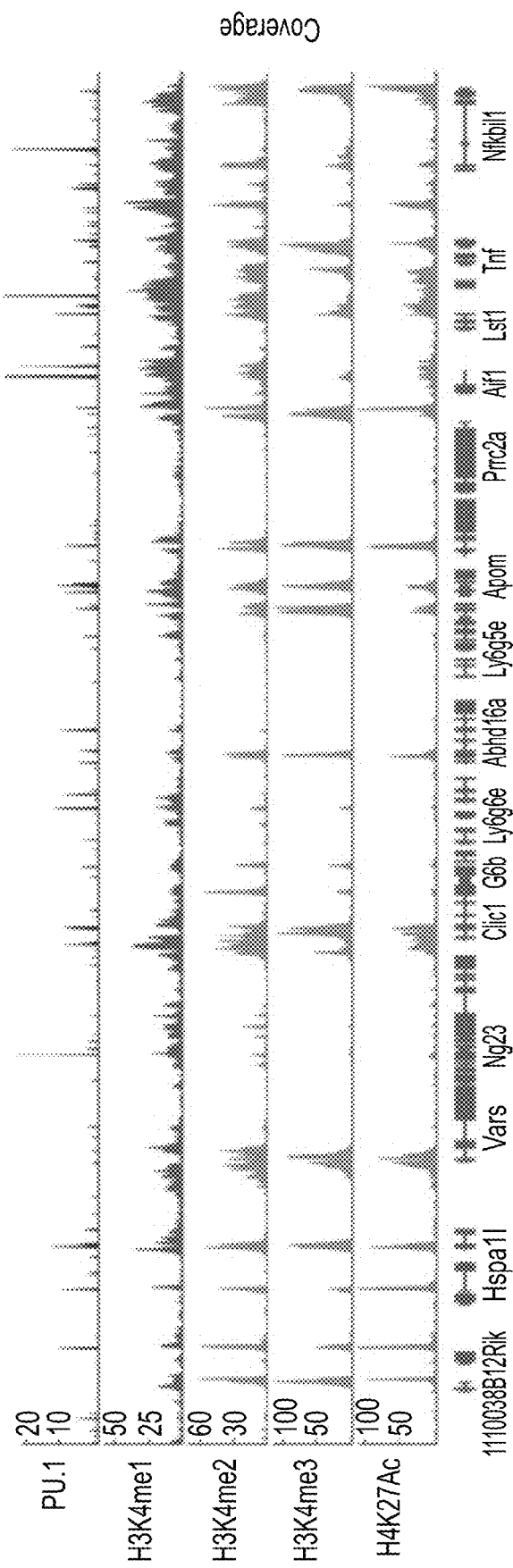
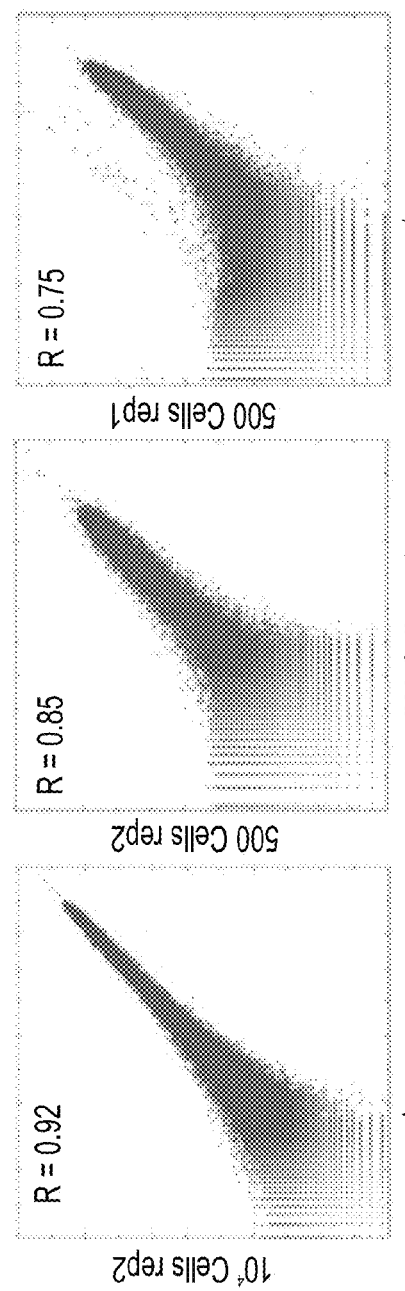
FIG. 1C
FIG. 1D

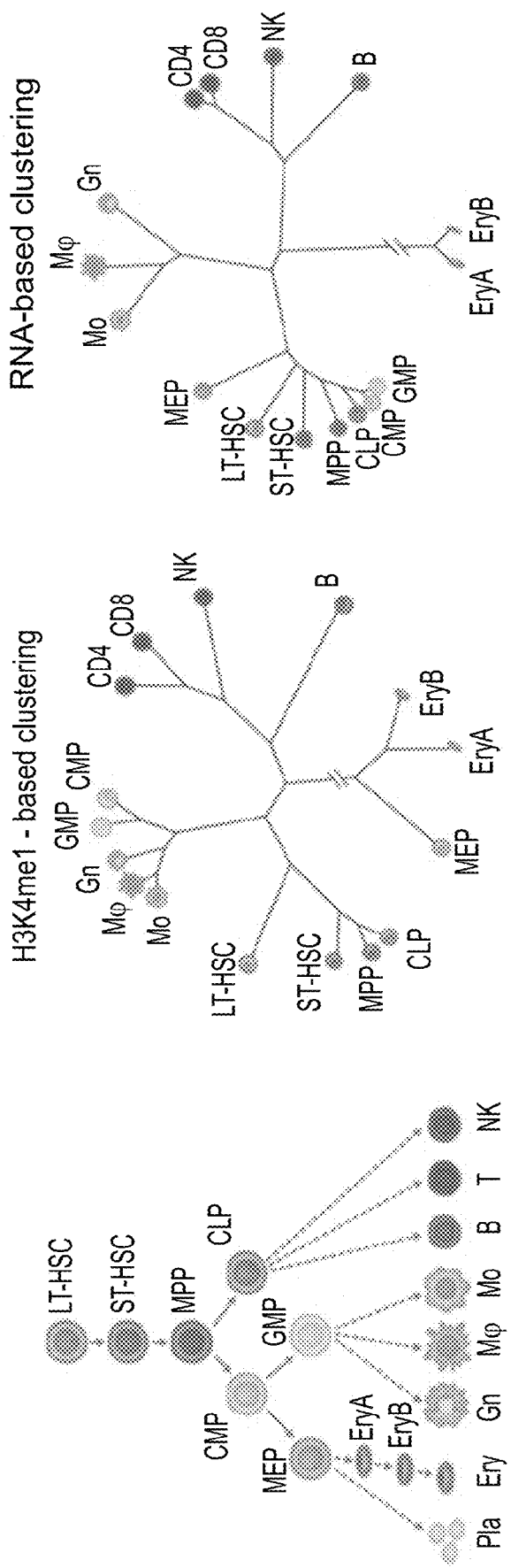

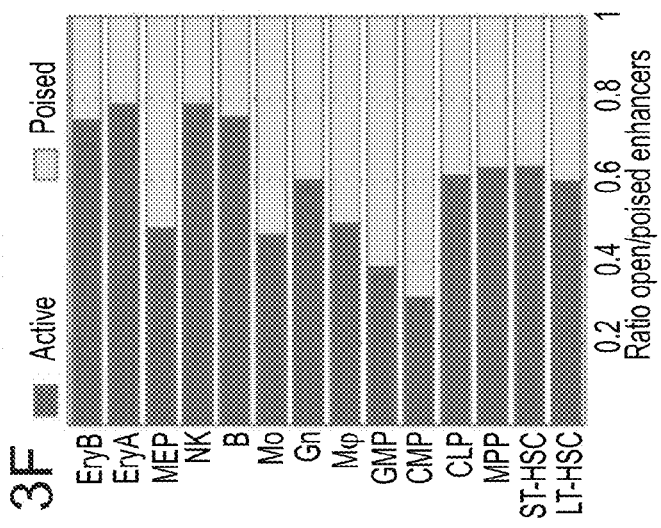
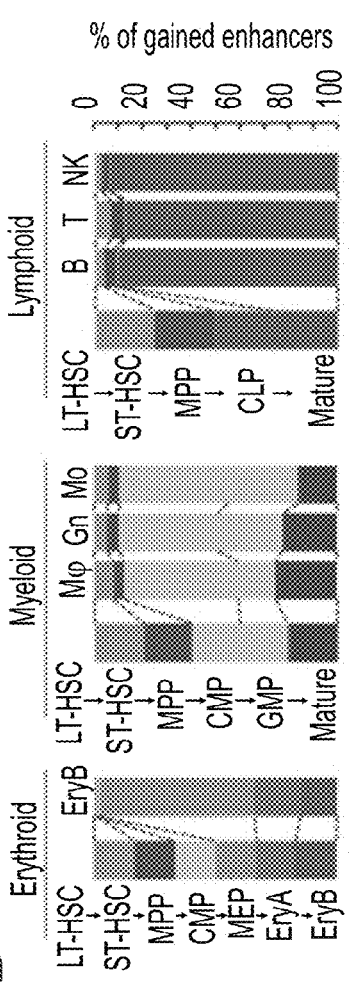
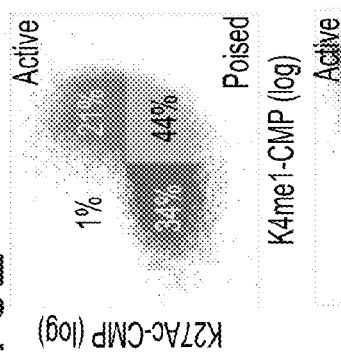
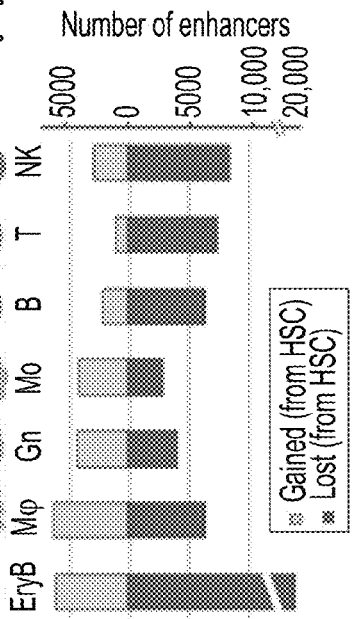
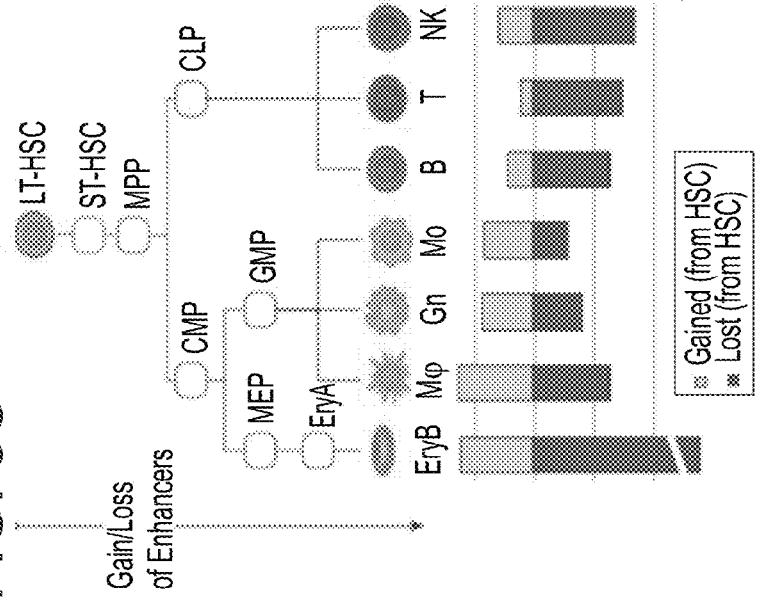
FIG. 3C   FIG. 3D   FIG. 3E   FIG. 3F

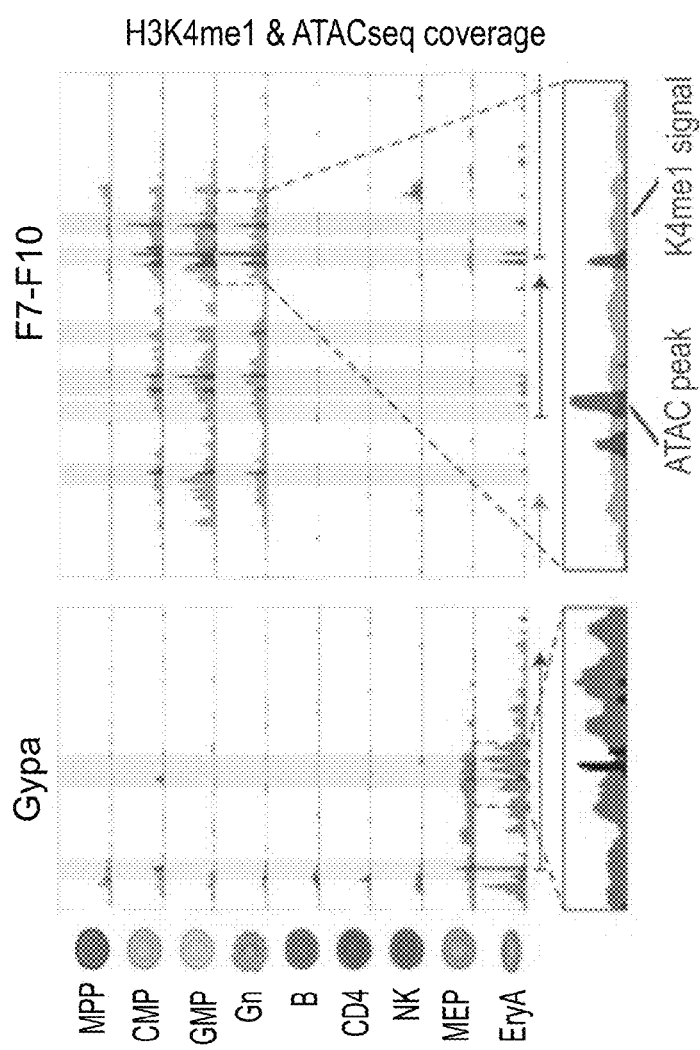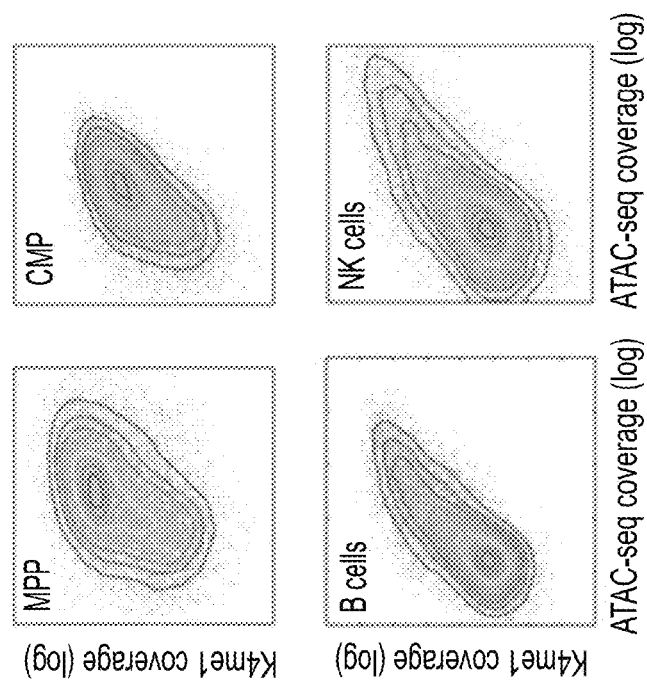
FIG. 4A
FIG. 4B

— METHODS AND KITS FOR ANALYZING DNA BINDING MOIETIES ATTACHED TO DNA

RELATED APPLICATIONS

This application is a National Phase of PCT Patent Application No. PCT/IL2015/050409 having International filing date of Apr. 16, 2015, which claims the benefit of priority under 35 USC § 119(e) of U.S. Provisional Patent Application No. 61/980,630 filed on Apr. 17, 2014. The contents of the above applications are all incorporated by reference as if fully set forth herein in their entirety.

SEQUENCE LISTING STATEMENT

The ASCII file, entitled 67703SequenceListing.txt, created on Oct. 12, 2016, comprising 3,363 bytes, submitted concurrently with the filing of this application is incorporated herein by reference.

FIELD AND BACKGROUND OF THE INVENTION

The present invention, in some embodiments thereof, relates to methods and kits for analyzing DNA binding moieties attached to DNA, and, more particularly, but not exclusively for analyzing histone binding in a cell.

Cell type specific functions and response rely on tight gene regulation, orchestrated by the chromatin landscape. The current dogma of cellular differentiation set forth more than half a century ago by Conrad Waddington presents a model of a progressive closing of the genome. According to this model, differentiation is a gradual transition from an open chromatin state in multipotent stem cells to a compacted chromatin state in differentiated cells. This model is supported by recent genome-wide histone modification analyzing presence or level of embryonic stem cells compared with terminally differentiated cells. Hematopoiesis is a paradigmatic differentiation process where a single hematopoietic stem cell gives rise to a large number of cell types (essentially the entire blood system) through a series of characterized intermediate progenitor cells. Chromatin regulation has a central role in hematopoiesis and mutations or loss of chromatin factors critically alter the hematopoietic outcome. Moreover, genome-wide chromatin analyzing presence or level of studies have revealed big differences in the histone modifications and TF binding maps in different mature immune cells. All these findings point to dynamic chromatin rearrangements at some point during hematopoiesis.

Comprehensive study of the chromatin events during hematopoiesis has been hampered by the low sensitivity and reproducibility for small cell numbers with current chromatin immunoprecipitation (ChIP) protocols. These protocols require several enzymatic steps with limited performance when the input DNA is below the nanogram range. While an average diploid mammalian cell has roughly 4-8 pg of DNA, losses following ChIP reduces the available DNA for analysis by 2-3 orders of magnitude, setting the lower limit for genome-wide chromatin analysis at 50,000 cells (T. S. Furey, *Nat. Rev. Genet.* 13, 840-852 (2012)).

Amplification of ChIP material partially alleviate this problem at the cost of introducing amplification biases (P. Shankaranarayanan et al., *Nat. Methods* 8, 565-567 (2011);

M. Garber et al., *Mol Cell* 47, 810-822 (2012). In addition, such amplification processes, make ChIP protocols laborious and bias prone.

Additional background art includes Blecher Gonen et al., *Nature Protocols*, 8, 539-554 (2013), US Patent Application No. 20140024052, WO 2013134261 and WO 2002014550.

SUMMARY OF THE INVENTION

According to an aspect of some embodiments of the present invention there is provided a method of analyzing DNA which, in a cell, is bound to a DNA binding moiety, the method comprising:
(a) obtaining at least two samples of complexes of DNA bound to a DNA binding moiety;
(b) isolating the complexes on a solid support;
(c) labeling the DNA of the complexes, wherein the labeling distinguishes between the complexes of the first of the at least two samples and the complexes of the second of the at least two samples;
(d) pooling the at least two samples of complexes; and
(e) isolating the complexes using an agent which specifically binds to the DNA binding moiety; and
(f) analyzing the DNA of the complexes.

According to an aspect of some embodiments of the present invention there is provided a method of analyzing DNA which, in a cell, is bound to a DNA binding moiety, the method comprising:
(a) obtaining at least two samples of complexes of DNA bound to a DNA binding moiety;
(b) shearing the DNA by sonication;
(c) labeling the DNA of the complexes, wherein the labeling distinguishes between the complexes of the first of the at least two samples and the complexes of the second of the at least two samples;
(d) pooling the at least two samples of complexes; and
(e) isolating the complexes using an agent which specifically binds to the DNA binding moiety; and
(f) analyzing the DNA of the complexes.

According to an aspect of some embodiments of the present invention there is provided a kit for chromatin immunoprecipitation comprising:
(i) an agent for immobilizing at least 50% of the chromatin of a cell;
(ii) at least one antibody which specifically binds to a subgroup of the chromatin; and
(iii) a plurality of barcode DNA sequences.

According to an aspect of some embodiments of the present invention there is provided a kit for immunoprecipitating a DNAprotein complex comprising:
(i) a Tagment DNA enzyme; and at least one of
(ii) at least one antibody which specifically binds to the protein of the DNA-protein complex; and
(iii) a DNA labeling agent.

According to an aspect of some embodiments of the present invention there is provided a kit for immunoprecipitating a DNA-protein complex comprising:
(i) at least one agent selected from the group consisting of an RNA polymerase, a DNAse and a reverse transcriptase; and
(ii) at least one antibody which specifically binds to the protein of the DNA protein complex.

According to some embodiments of the invention, the labeling is effected using a tagment DNA enzyme.

According to some embodiments of the invention, step (b) is effected using an antibody attached to the solid support.

According to some embodiments of the invention, the analyzing comprises sequencing the DNA.

According to some embodiments of the invention, the method further comprises amplifying the DNA following step (e) and prior to step (f).

According to some embodiments of the invention, the method further comprises analyzing the DNA binding moiety of the complex.

According to some embodiments of the invention, the first sample is a first cell type and the second sample is a second cell type.

According to some embodiments of the invention, the complexes are crosslinked.

According to some embodiments of the invention, the labeling is effected at the 5' and the 3' end of the DNA.

According to some embodiments of the invention, the labeling comprises a DNA barcode.

According to some embodiments of the invention, the DNA is no longer than 500 bases.

According to some embodiments of the invention, the DNA binding moiety is a DNA binding protein.

According to some embodiments of the invention, the DNA binding protein is a histone.

According to some embodiments of the invention, the DNA binding protein is a transcription factor.

According to some embodiments of the invention, the DNA binding moiety is a drug.

According to some embodiments of the invention, the method further comprises immobilizing the complexes following step (b) and prior to step (c).

According to some embodiments of the invention, the agent is an antibody.

According to some embodiments of the invention, the agent is attached to a solid support.

According to some embodiments of the invention, the kit further comprises an agent for immobilizing at least 50% of the chromatin of a cell.

According to some embodiments of the invention, the kit further comprises at least one agent selected from the group consisting of an RNA polymerase, a DNAse and a reverse transcriptase.

According to some embodiments of the invention, the agent is an antibody which specifically binds to a histone selected from the group consisting of H2, H3 and H4.

According to some embodiments of the invention, the agent is a filter.

According to some embodiments of the invention, the further comprises a plurality of barcode DNA sequences.

According to some embodiments of the invention, the at least one antibody specifically binds to a post-translationally modified histone.

According to some embodiments of the invention, the post-translationally modified histone is a methylation or acetylation.

According to some embodiments of the invention, the antibody specifically binds to a modification selected from the group consisting of H3K4me1, H3K4me2, H3K4me3 and H3K27ac.

According to some embodiments of the invention, the kit further comprises a solid support for immobilizing the at least one antibody.

According to some embodiments of the invention, the kit further comprises at least one component selected from the group consisting of a crosslinker, a protease enzyme and a ligase.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 2C, 2D:
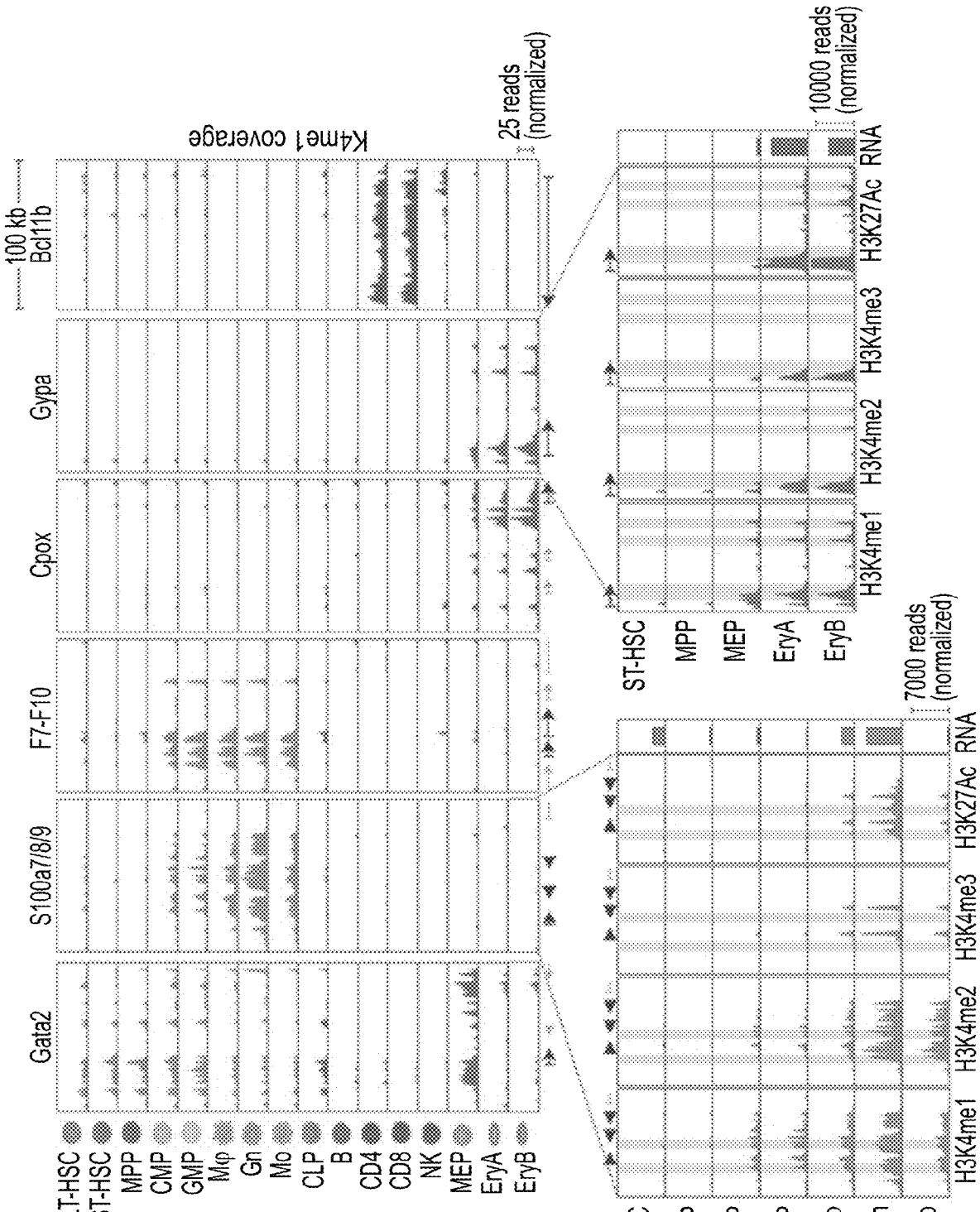

FIGS. 1A-D Indexing-first Chromatin ImmunoPrecipitation for profiling histone modifications and TF binding. (A) Schematic diagram of the iChIP approach to chromatin immunoprecipitation involving an initial chromatin barcoding step prior to ChIP with the desired antibody. (B) Normalized H3K4me3 profiles of peaks found in a 100 Kb region in the TNF locus (genes are indicated below) obtained with iChIP of decreasing amounts of bone-marrow derived dendritic cells (BMDC). Top, in red, H3K4me3 profile obtained using conventional ChIP with 20 million cells (15). Below, in shades of blue, H3K4me3 profiles obtained with iChIP. (C) Normalized profiles of PU.1, H3K4me1, H3K4me2, H3K4me3 and H3K27ac found in a 250 Kb region in the TNF locus obtained with iChIP with $10^4$ BMDC. (D) Scatter plots showing correlation between representative HK4me3 iChIP replicates. From left to right: correlation between $10^4$ cell replicates, 500 cell replicates, and a 500 compared to $10^4$ cells.

FIGS. 2A-D. Chromatin dynamics in hematopoiesis. (A) Schematic diagram of the hematopoietic differentiation stages included in this study (platelets are displayed, but were not included). Dashed-arrow indicates intermediate progenitors not measured in this study. Color code: green for multipotent progenitors, orange for myeloid lineage (including the oligopotent progenitors CMP and GMP), blue for lymphoid lineage, red for erythroid lineage. (B) Clustering dendrogram of cell types based on H3K4me1 profiles (left) and RNA-seq levels (right) showing the differential association of lineage progenitors (CMP, GMP, MEP). (C) Representative examples of H3K4me1 signal (cell types labeled at left) in several loci, (from left to right): Gata 2 for progenitors, F7-F10 and S100a8 for myeloid lineage, Gypa and Cpox for erythroid lineage, Bc111b for T cells. Displayed are normalized reads coverage in a 100 Kb region around the gene body. (D) Profiles of H3K4me1, H3K4me2, H3K4me3, H3K27ac modifications and RNA expression levels in two lineage specific gene loci: S100a8 in (myeloid) and Gypa (erythroid). Displayed are profiles for the lineage-specific cell types and multipotent progenitor cells over a 100 Kb region around the gene body. Putative lineage specific enhancers are shadowed in blue. Lineage specific genes are indicated below (black), as well as other genes in the loci (light gray).

FIGS. 3A-F. Hematopoiesis progresses through gain and loss of lineage specific enhancers (A) Heatmap showing 48,415 hematopoiesis enhancers clustered with K-means (K=9) of average reads count within H3K4me1 regions (16) annotated with the genomic sequence conservation of the enhancers, right (blue scale; (16)). Annotations for important lineage specific genes loci are shown on the left. (B) Schematic tree-view of three representative enhancer clusters; progenitors (V), myeloid (VI) and erythroid (IX). Color fill represents stages with H3K4me1 mark at the enhancer (C) Bar plot showing the number of enhancers gained (top, light gray) and lost (bottom, dark gray) during the development from HSC to mature hematopoietic cells along each lineage. (D) Bar plot showing the percent of de novo enhancers (from C) established at each developmental stage from HSC to mature hematopoietic cells. (E) Scatter plots showing H3K27ac signal versus H3K4me1 signal in both CMPs and EryA cells. Active enhancers (H3K4me1 positive, H3K27ac positive) are colored in red, poised enhancers (H3K4me1 positive, H3K27ac negative) in light gray, inactive enhancers (H3K4me1 negative, H3K27Ac negative) in blue. (F) Proportions of active (red) and poised (light gray) enhancers in each of the cell types studied.

FIGS. 4A-F. Lineage-specific enhancers are associated with transcription factor cohorts (A) ATAC-seq signal co-occurs temporally with H3K4me1 in lineage-specific enhancers. Shown are normalized profiles in 9 hematopoietic cells for ATAC-seq (Black) and H3K4me1 in erythroid-specific, Gypa (Red) and myeloid-specific, F7-10 loci (Orange). Displayed are peaks found in a 100 Kb region around the gene body. Putative enhancers (K4me1) shadowed in blue, transcriptional start site shadowed in red. Zoom in of ATAC-seq peak is shown below. (B) Scatter plot showing correlation between H3K4me1 signal and enhancer restricted ATAC-seq signal in four cell types: B cells, NK, MPP and CMPs (colors represent density or points). (C) Heatmap showing the p-values of transcription factor motif (Kolmagorov-Smirnov test) for the indicated cell-type-specific enhancers (16). Red indicates significant enrichment (p<1e-5) of motif associated to the labeled TF, green indicates motif depletion (p<1e-5). White indicates either no significant enrichment or no RNA expression. (D) Bar plots showing gene expression profiles across the hematopoietic cell types for representative transcription factors (from C). (E) Schematic of the hematopoietic tree showing the representative transcription factors regulating the lineage enhancers at each cell type as predicated by the logistic model. (F) Schematic of establishment of lineage-specific enhancers in the myeloid lineage by a conventional mechanism (right) as well as via TF-mediated establishment of de novo enhancers (left).

DESCRIPTION OF SPECIFIC EMBODIMENTS OF THE INVENTION

The present invention, in some embodiments thereof, relates to methods and kits for analyzing DNA binding moieties attached to DNA, and, more particularly, but not exclusively for analyzing histone binding in a cell.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Current chromatin immunoprecipitation (ChIP) protocols require several enzymatic steps with limited performance when the input DNA is below the nanogram range. While an average diploid mammalian cell has roughly 4-8 pg of DNA, losses following ChIP reduces the available DNA for analysis by 2-3 orders of magnitude, setting the lower limit for genome-wide chromatin analysis at 50,000 cells. Amplification of ChIP material partially alleviates this problem at the cost of introducing amplification biases.

The present inventors have now devised a novel method for analyzing chromatin derived from a small numbers of cells. In this protocol, barcoding is performed directly on the total cellular chromatin, thereby avoiding the low input enzymatic reactions occurring in conventional ChIP. Importantly, this enables multiple chromatin-barcoded samples to be pooled for ChIP in the same well, further reducing initial input requirements and increasing cross-sample reproducibility. To minimize centrifugation steps, cells are cross-linked before sorting, and DNA fractionation. Then, the sheared chromatin is immobilized and indexed. The indexed chromatin is released and pooled with chromatin from other samples. Finally, ChIP is performed with the desired antibody, and a single chromatin-barcoded pool can be split to multiple ChIPs for profiling various chromatin modifications.

The present inventors showed that this protocol is highly reproducible for low cell numbers (a few hundred cells) while increasing the sensitivity and throughput (FIGS. 1A-D). Whilst reducing the present invention to practice, the present inventors barcoded decreasing amounts (10,000 to 500 cells) of chromatin isolated from bone-marrow-derived dendritic cells (BMDCs), in triplicate, and performed ChIP on the barcoded chromatin with an antibody for mono and tri-methylated histone H3 lysine 4 (H3K4me1 and H3K4me3) (FIGS. 1B-D). They confirmed reproducibility of H3K4me3 peaks between replicates of 10,000 cells (r=0.95) down to 500 cells (r=0.85). The ChIP profiles they obtained correlated with conventional ChIP-seq on 10 million BMDCs (r=0.92).

Accordingly, the present inventors propose that their ChIP protocol may be used to profile other histone modifications and transcription factors binding sites for low cell numbers (FIGS. 1C-D).

Thus, according to one aspect of the present invention there is provided a method of analyzing DNA which, in a cell, is bound to a DNA binding moiety, the method comprising:
(a) obtaining at least two samples of complexes of DNA bound to a DNA binding moiety;
(b) labeling the DNA of the complexes, wherein the labeling distinguishes between the complexes of the first of the at least two samples and the complexes of the second of the at least two samples;
(c) pooling the at least two samples of complexes; and
(d) isolating the complexes using an agent which specifically binds to the DNA binding moiety; and
(e) analyzing the DNA of the complexes.

The DNA which is analyzed may be derived from a eukaryotic or a prokaryotic cell. According to one embodiment, the DNA is derived from a mammalian cell (e.g. human). In the cell, (i.e. in the in-vivo environment) from where it is derived, the DNA may be bound permanently or temporarily to the DNA binding moiety.

According to a particular embodiment, the method is not carried out using a microfluidic device.

As used herein the phrase "DNA binding moiety" refers to an agent which binds to DNA (in a sequence specific or non-specific manner. The DNA binding moiety may bind to DNA via intercalation, groove binding and/or covalent binding.

In one embodiment, the DNA binding moiety is a DNA binding polypeptide or peptide.

In another embodiment, the DNA binding moiety is a drug (e.g. a small molecule agent).

DNA-binding polypeptides include transcription factors which modulate the process of transcription, various polymerases, nucleases which cleave DNA molecules, and histones which are involved in chromosome packaging and transcription in the cell nucleus. DNA-binding proteins can incorporate such domains as the zinc finger, the helix-turn-helix, and the leucine zipper (among many others) that facilitate binding to nucleic acid.

According to a particular embodiment, the DNA binding protein is a histone.

The following is a list of human histone proteins which may be analyzed according to the methods described herein.

TABLE 1

| Super family | Family | Sub-family | Members |
|---|---|---|---|
| Linker | H1 | H1F | H1F0, H1FNT, H1FOO, H1FX |
| | | H1H1 | HIST1H1A, HIST1H1B, HIST1H1C, HIST1H1D, HIST1H1E, HIST1H1T |
| Core | H2A | H2AF | H2AFB1, H2AFB2, H2AFB3, H2AFJ, H2AFV, H2AFX, H2AFY, H2AFY2, H2AFZ |
| | | H2A1 | HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM |
| | | H2A2 | HIST2H2AA3, HIST2H2AC |
| | H2B | H2BF | H2BFM, H2BFS, H2BFWT |
| | | H2B1 | HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO |
| | | H2B2 | HIST2H2BE |
| | H3 | H3A1 | HIST1H3A, HIST1H3B, HIST1H3C, HIST1H3D, HIST1H3E, HIST1H3F, HIST1H3G, HIST1H3H, HIST1H3I, HIST1H3J |
| | | H3A2 | HIST2H3C |
| | | H3A3 | HIST3H3 |
| | H4 | H41 | HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L |
| | | H44 | HIST4H4 |

Examples of histone modifications in transcription regulation are summarized in Table 2 herein below.

Step 1: Obtaining at Least Two Samples of Complexes of DNA Bound to the DNA Binding Moiety.

The samples are cellular samples. Obtaining cellular samples is carried out according to methods known in the art. The cells may be obtained from a body fluid (e.g. blood) or a body tissue. The cells may be obtained from a subject (e.g. mammalian subject) or may be part of a cell culture. The cells may arise from a healthy organism, or one that is diseased or suspected of being diseased. According to a particular embodiment, each sample comprises cells of a particular cell type (i.e. a homogeneous population of cells). Thus, for example one of the samples may comprise granulocytes, another of the samples may comprise macrophages, another of the samples may comprise monocytes etc. The samples of a single cell type may be obtained using methods known in the art—for example by FACs sorting. According to still another embodiment, each sample comprises cells from a particular source (e.g. from a particular subject).

According to further embodiments, each sample comprises 100-10,000 cells, 100-5000 cells, 100-2,500 cells, 100-1,000 cells, 100-7,500 cells, 100-5,000 cells, 100-2,500 cells, 100-1000 cells, 100-750 cells, 200-750 cells (for example about 500 cells).

According to one embodiment, the cells are reversibly crosslinked in order to ensure that DNA binding moieties that are bound to DNA in the in vivo environment (i.e in the cell) remain bound during the immunoprecipitation procedure. Agents that may be used for reversible cross-linking include but are not limited to formaldehyde or ultraviolet light. Additional agents include, but are not limited to homobifunctional compounds difluoro-2,4-dinitrobenzene (DFDNB), dimethyl pimelimidate (DMP), disuccinimidyl suberate (DSS), the carbodiimide reagent EDC, psoralens including 4,5',8-trimethylpsoralen, photo-activatable azides such as $^{125}$I(S-[2-(4-azidosalicylamidolethylthio]-2-thio-pyridine) otherwise known as AET, (N-[4-(p-axidosalicy-lamido)butyl]-3'[2'-pridyldithiolpropionamide) also known as APDP, the chemical cross-linking reagent Ni(II)-NH2-Gly-Gly-His-COOH also known as Ni-GGH, sulfosuccin-imidyl 2-[(4-axidosalicyl) amino]ethyl]-1,3-dithiopropi-onate) also known as SASD, (N-14-(2-hydroxybenzoyl)-N-11(4-azidobenzoyl)-9-oxo-8,11,14-triaza-4,5-ditheatetradec anoate).

The complexes of this aspect of the invention are isolated from the cells. Thus, the present invention contemplates lysing the cells so as to release the complexes from within. Cell lysis may be performed using standard protocols which may be successfully implemented by those skilled in the art including mechanical disruption of cell membranes, such as by repeated freezing and thawing, homogenization, sonication, pressure, or filtration and the use of enzymes and/or detergents (e.g. SDS). For the purposes of chromosomal immunoprecipitation it is important that metal chelators

TABLE 2

| Type of modification | Histone | | | | | | | |
|---|---|---|---|---|---|---|---|---|
| | H3K4 | H3K9 | H3K14 | H3K27 | H3K79 | H3K36 | H4K20 | H2BK5 |
| mono-methylation | activation | activation | | activation | activation | | activation | activation |
| di-methylation | | repression | | repression | activation | | | |
| tri-methylation | activation | repression | | repression | activation, repression | activation | | repression |
| acetylation | | | activation | activation | activation | | | | such as EDTA and EGTA as well as protease inhibitors be added to the reaction to prevent degradation of protein DNA complexes.

According to a particular embodiment, the DNA of the complexes is no longer than 1000 base pairs, and more preferably no longer than 500 base pairs. If the DNA in the sample is longer, the present invention contemplates a step of shearing or cleaving the DNA. This may be effected by sonication for various amounts of time. The precise time for sonication depends on the cells in the sample and determining the time is within the expertise of one skilled in the art. Examples of sonicators that may be used include the NGS Bioruptor Sonicator (Diagenode) or Branson model 250 sonifier/sonicator as well as restriction enzyme digestion by frequent as well as rare-cutting enzymes including, but not limited to, Ace I, Aci I, Acl I, Afe I, Afl It, Afl El Age I, Ahd I, Alu I, Alw I, AlwN I, Apa I, ApaL I, Apo I, Asc I, Ase I, Ava I, Ava II, Avr II, Bae I, BamH I, Ban I, Ban π, Bbs I, Bbv I, BbvC I, BceA I, Beg I, BciV I, Bel I, Bfa I, BfrB I, Bgl I, Bgl II, Blp I, Bmr I, Bpm I, BsaA I, BsaB I, BsaH I, Bsa I, BsaJ I, BsaW I, BsaX I, BseR I, Bsg I, BsiE I, BsiHKA I, BsiW I, Bsl I, BsmA I, Bs B I, BsmF I, Bsm I, BsoB I, Bspl2861, BspD I, BspE I, BspH I, BspM I, BsrB I, BsrD I, BsrF I, BsrG I, Bsr I, BssH II, BssK I, BssS I, BstAP I, BstB I, BstE II, BstF5 I, BstN I, BstU I, BstX I, BstY I, BstZ171, Bsu361, Btg I, Btr I, Bts I, Cac8 I, Cla I, Dde I, Dpn I, Dpn II, Dra I, Dra HI, Drd I, Eae I, Eag I, Ear I, Eci I, EcoN I, EcoO109 I, EcoR I, EcoR V, Fau I, Fnu4H I, Fok I, Fse I, Fsp I, Hae π, Hae Iὒ, Hga I, Hha I, Hinc II, Hind m, Hinf I, HinPl I, Hpa I, Hpa II, Hpyl88 I, Hpyl88 IE, Hpy99 1, HpyCH4iπ, HpyCH4IV, HpyCH4V, Hph I, Kas I, Kpn I, Mbo I, Mbo II, Mfe I, Mlu I, Mly I, Mnl I, Msc I, Mse I, Msl I, MspAl I, Msp I, Mwo I, Nae I, Nar I, Nci I, Nco I, Nde I, NgoM IV, Nhe I, Nla in, Nla IV, Not I, Nru I, Nsi I, Nsp I, Pac I, PaeR7 1, Pci I, PflF I, PflM I, Pie I, Pme I, Pml I, PpuM I, PshA I, Psi I, PspG I, PspOM I, Pst I, Pvu I, Pvu H, Rsa I, Rsr II, Sac I, Sac π, Sal I, Sap I, Sau3A I, Sau96 1, Sbf I, Sea I, ScrF I, SexA I, SfaN I, Sfc I, Sfi I, Sfo, SgrA I, Sma I, Sml I, SnaB I, Spe, Sph I, Ssp I, Stu I, Sty I Swa I, Taq I, Tfi I, Tli I, Tse I, Tsp45 I, Tsp509 I, TspR I, Tthl 111, Xba I, Xcm I, Xho I, Xma I and Xmn I.

According to a particular embodiment, the enzyme is not MNase.

Other enzymes that may be used are further described herein below.

Step 2: Labeling the DNA of the complexes.

According to one embodiment, the labeling is performed following immobilization of the isolated DNA complexes. Any form of immobilization is conceived by the present inventors as long as it does not interfere with the labeling of the DNA.

According to a particular embodiment, the complexes are not immobilized in microfluidic droplets.

According to one embodiment, the complexes are immobilized on a solid support. Examples of solid supports contemplated by the present invention include, but are not limited to, sepharose, chitin, protein A cross-linked to agarose, protein G cross-linked to agarose, agarose cross-linked to other proteins, ubiquitin cross-linked to agarose, thiophilic resin, protein G cross-linked to agarose, protein L cross-linked to agarose and any support material which allows for an increase in the efficiency of purification of protein/DNA complexes.

According to another embodiment, the complexes are immobilized on a solid support using an antibody that binds to at least 30%, more preferably 40%, more preferably 50% of the complexes in the sample. The antibody of this aspect of the present invention may be polyclonal or monoclonal. The antibodies may bind to the full length proteins as well as against particular epitope amino acid subsets present within those proteins. The antibodies may be of any origin (e.g. rabbit, goat origin, humanized).

Thus, for example when the sample comprises chromatin, the antibody may specifically bind to an H2, H3 or H4 histone. According to a particular embodiment the antibody specifically binds to H3. Antibodies that recognize histones are commercially available from various sources including for example Abcam and Pierce. For immobilization, the antibodies are attached to a solid support including but not limited to magnetic beads. Other solid phase supports contemplated by the present invention include, but are not limited to, sepharose, chitin, protein A cross-linked to agarose, protein G cross-linked to agarose, agarose cross-linked to other proteins, ubiquitin cross-linked to agarose, thiophilic resin, protein G cross-linked to agarose, protein L cross-linked to agarose and any support material which allows for an increase in the efficiency of purification of protein/DNA complexes.

Methods of attaching antibodies to solid supports are known in the art. For example, linkage of antibodies to solid phase support magnetic beads may be accomplished via standard protocol (Dynal Corporation product information and specifications) and those known and skilled in the art are capable of establishing this linkage successfully. Beads are washed briefly in an appropriate buffer (e.g. phosphate buffered saline (PBS), pH 7.4). About 0.1-1.5 µg of antibody are added per ml of beads, the volume adjusted and the mixture incubated for a suitable length of time (e.g. 12-24 hours at 4° C.). The beads are subsequently collected via a magnet and the supernatant removed. The beads may be washed at least one more time (e.g. in 10 mM Tris-HCl, pH 7.6) for an additional 16-24 hours the bead/antibody complex is ready for immunoprecipitation of protein/DNA complexes.

Magnetic beads contemplated by the present invention include those created by Dynal Corporation such as for example Dynabeads M-450 Tosylactivated (Dynal Corporation). Other Dynabeads M-450 uncoated, Dynabeads M-280 Tosylactivated, Dynabeads M-450 Sheep anti-Mouse IgG, Dynabeads M-450 Goat anti-Mouse IgG, Dynabeads M-450 Sheep anti-Rat IgG, Dynabeads M-450 Rat anti-Mouse IgM, Dynabeads M-280 sheep anti-Mouse IgG, Dynabeads M-280 Sheep anti-Rabbit IgG, Dynabeads M-450 sheep anti-Mouse IgG1, Dynabeads M-450 Rat anti-Mouse IgG1, Dynabeads M-450 Rat anti-Mouse IgG2a, Dynabeads M-450 Rat anti-Mouse IgG2b, Dynabeads M-450 Rat anti-Mouse IgG3. Other magnetic beads which are also contemplated by the present invention as providing utility for the purposes of immunoprecipitation include streptavidin coated Dynabeads.

An alternative method of attaching antibodies to magnetic beads or other solid phase support material contemplated by the present invention is the procedure of chemical cross-linking. Cross-linking of antibodies to beads may be performed by a variety of methods but may involve the utilization of a chemical reagent which facilitates the attachment of the antibody to the bead followed by several neutralization and washing steps to further prepare the antibody coated beads for immunoprecipitation. Yet another method of attaching antibodies to magnetic beads contemplated by the present invention is the procedure of UV cross-linking. A third method of attaching antibodies to magnetic beads contemplated by the present invention is the procedure of enzymatic cross-linking.

A column support fixture rather than beads may be successfully employed for purposes of solid phase. In addition, support fixtures such as Petri dishes, filters, chemically coated test tubes or eppendorph tubes which may have the capability to bind antibody coated beads or other antibody coated solid phase support materials may also be employed by the present invention.

Labeling of DNA:

Labeling may be effected on the 3' end of the DNA, the 5' end of the DNA or on both the 3' and 5' end of the DNA. According to a particular embodiment, an identical tag is used to label the 3' and 5' end of the DNA. Labels include fluorescent dyes, quantum dots, magnetic particles, metallic particles, and colored dyes. Generic labels include labels that bind non-specifically to nucleic acids (e.g., intercalating dyes, nucleic acid groove binding dyes, and minor groove binders) or proteins. Examples of intercalating dyes include YOYO-1, TOTO-3, Syber Green, and ethidium bromide.

According to a particular embodiment, the DNA is labeled via a ligation reaction to an adapter that contains a barcode sequence. In one embodiment, the adapter comprises a Solexa adapter. In one embodiment, the adapter comprises an Illumina adapter. The DNA may also be labeled using an enzyme (e.g. Tn5 transposase, Tagment DNA enzyme) that mediates both the fragmentation of double-stranded DNA and ligates synthetic oligonucleotides may be used.

The ligation may be a blunt-ended ligation or using a protruding single stranded sequence (e.g. the sequence may first be A-tailed). The adapter may comprise additional sequences e.g. a sequence recognizable by a PCR primer, sequences which are necessary for attaching to a flow cell surface (P5 and P7 sites), a sequence which encodes for a promoter for an RNA polymerase (as further described herein below) and/or a restriction site. In one embodiment, the adaptor does not comprise sequences which encode a restriction enzyme site. The barcode sequence may be used to identify a particular molecule, sample or library. The barcode sequence may be between 3-400 nucleotides, more preferably between 3-200 and even more preferably between 3-100 nucleotides. Thus, the barcode sequence may be 6 nucleotides, 7 nucleotides, 8, nucleotides, nine nucleotides or ten nucleotides. The barcode is typically 4-15 nucleotides.

RNA polymerase promoter sequences are known in the art and include for example T7 RNA polymerase promoter sequence—e.g. SEQ ID NO: 10 (CGATTGAGGCCGG-TAATACGACTCACTATAGGGGC).

For a population of adapters to be used to identify a population of cells, the identification sequence of the adapter differs according to the cell type while the rest of the adapter is identical. Since each cell-type is labeled with an adapter containing a different identification sequence, the nucleic acids arising from these cells may be distinguished.

Removal of non-ligated adaptors may be effected using any method known in the art (for example 10 mM TrisCl). The buffer for removal of non-ligated adaptors may also comprise protease inhibitors.

If the complexes were immobilized prior to the labeling stage, the next stage comprises release of the immobilized complexes. The present inventors contemplate any method of releasing the complexes so long as the DNA of the complexes remains labeled. Methods include use of detergents (e.g. DTT, Sodium Deoxycholate), high salt (e.g. 200-700 mM, e.g. 500 mM salt, NaCl) and/or heat (e.g. about 37° C.). Protease inhibitors may also be included in the buffer. Preferably, the method used releases more than 40% of the complexes, more preferably more than 50% of the complexes, and even more preferably more than 60% of the complexes.

Step 3: Pooling the Complexes

Following labeling (and release from the immobilizing agent), the samples are then pooled. The complexes may be purified at this stage and/or concentrated. This may be effected using any method known in the art including ultracentrifugation (e.g. using a centricon with a 50 kDa cutoff). Additionally, or alternatively, the complexes may be washed prior to the next stage to ensure that the complexes are capable of binding to the agent. For example, the final salt and detergent level should be compatible with antibody integrity. Thus, for example, the detergent level should be less than about 1 mM and the salt concentration (for example NaCl) should be less than about 150 mM. An exemplary buffer which may be used to incubate the complexes is as follows: 10 mM Tris-HCl pH 8.0, 140 mM NaCl, 1% Triton X-100, 0.1% SDS, 0.1% DOC, 1 mM EDTA, 1× Protease Inhibitors.

Step 4: Isolating the Complexes Using an Agent which Specifically Binds to the DNA Binding Moiety Agents which bind to DNA binding moieties are typically antibodies as described herein above.

According to one embodiment, the antibody binds specifically to a transcription factor. Exemplary transcription factors include but are not limited to those described in WO 2002014550, the contents of which is incorporated herein by reference.

According to another embodiment, the antibody binds to a modified histone. Examples of histone modifications that may be studied include acetylation, methylation, ubiquitylation, phosphorylation and sum.oylation. Thus, for example the antibody may bind specifically to H3K4me1, H3K4me2, H3K4me3 or H3K27Ac. Such antibodies are commercially available from a number of sources—for example Abcam.

Upon sufficient isolation of protein/DNA complexes utilizing the above described immunoprecipitation technologies described, the complexes are reverse cross-linked so as to release the DNA fragments for further analysis. Those known and skilled in the art are capable of successfully reversing cross-linkages via conventional chromosomal immunoprecipitation protocols. Reversal of cross-linkages is accomplished through an incubation of the isolated protein/DNA complexes at high temperatures, preferably above 50° C. for at least 6 hours, (e.g. 65° C. for about 8 hours). It is contemplated by the present invention that reversal of cross-linkages through chemical methods such as alkali treatment as well as UV or enzymatic manipulation may be implemented successfully and are covered by the presently described invention for the purposes of the present invention, as long as the DNA of the complex is not altered in any way such that it cannot undergo sequence analysis.

In order to increase sensitivity, the released (reverse crosslinked) DNA may undergo a stage of in vitro transcription (according to this embodiment, the adaptor sequence in the labeling stage should comprise an RNA polymerase binding site, as further described herein above). The DNA is incubated with an RNA polymerase (e.g. T7), ribonucleotide triphosphates, preferably in a buffer system that includes DTT and to magnesium ions. The sample is then incubated with a DNAse to remove the DNA from the sample.

For further enhancement of sensitivity, an additional step may be carried out to ensure that both ends of the molecule are bar-coded. Thus, the present invention contemplates ligating another sequencing adaptor to the in-vitro synthesized RNA molecules using an RNA ligase enzyme (e.g. T4

RNA ligase). An exemplary buffer for performing this reaction is as follows: 9.5% DMSO, 1 mM ATP, 20% PEG8000 and 1 U/μl T4 ligase in 50 mM Tris HCl pH7.5, 10 mM MgCl$_2$ and 1 mM DTT.

Reverse transcription may then be carried out to convert the synthesized RNA into DNA. An exemplary reverse transcriptase enzyme is the Affinity Script RT enzyme (commercially available from Agilent). An exemplary reaction mix may contain a suitable buffer supplemented DTT, dNTPs, the RT enzyme and a primer complementary to the ligated adapter.

The DNA may be sequenced using any method known in the art—e.g. massively parallel DNA sequencing, sequencing-by-synthesis, sequencing-by-ligation, 454 pyrosequencing, cluster amplification, bridge amplification, and PCR amplification, although preferably, the method comprises a high throughput sequencing method. Typical methods include the sequencing technology and analytical instrumentation offered by Roche 454 Life Sciences™, Branford, Conn., which is sometimes referred to herein as "454 technology" or "454 sequencing."; the sequencing technology and analytical instrumentation offered by Illumina, Inc, San Diego, Calif. (their Solexa Sequencing technology is sometimes referred to herein as the "Solexa method" or "Solexa technology"); or the sequencing technology and analytical instrumentation offered by ABI, Applied Biosystems, Indianapolis, Ind., which is sometimes referred to herein as the ABI-SOLiD™ platform or methodology.

Other known methods for sequencing include, for example, those described in: Sanger, F. et al., Proc. Natl. Acad. Sci. U.S.A. 75, 5463-5467 (1977); Maxam, A. M. & Gilbert, W. Proc Natl Acad Sci USA 74, 560-564 (1977); Ronaghi, M. et al., Science 281, 363, 365 (1998); Lysov, l. et al., Dokl Akad Nauk SSSR 303, 1508-1511 (1988); Bains W. & Smith G. C. J. Theor Biol 135, 303-307 (1988); Drnanac, R. et al., Genomics 4, 114-128 (1989); Khrapko, K. R. et al., FEBS Lett 256.118-122 (1989); Pevzner P. A. J Biomol Struct Dyn 7, 63-73 (1989); and Southern, E. M. et al., Genomics 13, 1008-1017 (1992). Pyrophosphate-based sequencing reaction as described, e.g., in U.S. Pat. Nos. 6,274,320, 6,258,568 and 6,210,891, may also be used.

Following sequencing, the DNA may be aligned with genomes, e.g., to determine which portions of the genome were epigenetically modified, e.g., via methylation. Analysis of the sequences may provides information relating to potential transcription factor binding sites and/or epigenetic profiling, as further described in the Examples section herein below.

Kits

Any of the compositions described herein may be comprised in a kit. In a non-limiting example the kit comprises the following components, each component being in a suitable container:
(i) an agent for immobilizing at least 50% of the chromatin of a cell (e.g. a filter, or an antibody which specifically binds to a histone selected from the group consisting of H2, H3 and H4).
(ii) at least one antibody which specifically binds to a subgroup of the chromatin; and
(iii) a plurality of barcode DNA sequences.

The kit may comprise additional components including, but not limited to an RNA polymerase, a DNAse and/or a reverse transcriptase. Additional components include a crosslinker, a protease enzyme, nucleotide triphosphates and/or a ligase. The kit may also comprise the appropriate buffers for carrying out the immunoprecipitation procedure described herein. Exemplary buffers are described herein above and in the Examples section herein below.

In another non-limiting example the kit comprises the following components, each component being in a suitable container:
(i) a Tagment DNA enzyme; and at least one of
(ii) at least one antibody which specifically binds to the protein of the DNA-protein complex; and
(iii) a DNA labeling agent (e.g. the adaptors which comprise the barcode sequences as described herein above).

The kit may comprise additional components including, but not limited to an RNA polymerase, a DNAse, nucleotide triphosphates and/or a reverse transcriptase. Additional components include a crosslinker, a protease enzyme and/or a ligase. The kit may also comprise the appropriate buffers for carrying out the immunoprecipitation procedure described herein. Exemplary buffers are described herein above and in the Examples section herein below.

In another non-limiting example the kit comprises the following components, each component being in a suitable container:
(i) at least one agent selected from the group consisting of an RNA polymerase, a DNAse and a reverse transcriptase; and
(ii) at least one antibody which specifically binds to the protein of the DNA protein complex.

Additional components include a crosslinker, nucleotide triphosphates, a protease enzyme and/or a ligase. The kit may also comprise the appropriate buffers for carrying out the immunoprecipitation procedure described herein. Exemplary buffers are described herein above and in the Examples section herein below.

According to particular embodiment, the kits of this aspect of the present invention do not comprise MNAse.

The containers of the kits will generally include at least one vial, test tube, flask, bottle, syringe or other containers, into which a component may be placed, and preferably, suitably aliquoted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

A kit will preferably include instructions for employing, the kit components as well the use of any other reagent not included in the kit. Instructions may include variations that can be implemented.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Cell Harvesting: FACS-Sorted cross-linked cells are collected in 5 ml FACS tubes containing 500 ul of fetal calf serum, diluted in 4 ml of iChIP Harvesting Buffer (12 mM TrisCl, 0.1×PBS, 6 mM EDTA, 1.2× Protease Inhibitors (Roche) and pelleted by centrifugation for 15 mm at 1000×G using a swing rotor with low acceleration and brake settings. Supernatant is removed leaving a 200 ul cover to avoid disturbing the cell pellet. Cells are re-suspended in the 200 ul buffer cover, transferred to 0.2 ml tubes in aliquots of 10,000-20,000 cells, then cells are pelleted at 1000×G for 15 mm using above settings. Supernatant is removed leaving 10 ul of buffer covering the cell pellet. Cells are frozen stored at −80 C.

Sonication: Cell aliquots are thawed on ice and 2 ul of 3% SDS is added to achieve a final concentration of 0.5% SDS. Cells are thoroughly re-suspended and lysed on ice for 10 mm Lysates were transferred into 0.1 ml Bioruptor Microtubes (Diagenode C30010015, Liege, Belgium) and the chromatin was sheared using an NGS Bioruptor Sonicator (Diagenode) at High Intensity and cycles of 30" ON/30" OFF. Sonication time was calibrated for the different cell types: 20 mM for MEPs, EryA and EryB; 25 min for CMPs; 30 mM for LT-HSC, ST-HSC, MPP and GMPs; 40 mM for Granulocytes, Monocytes and Macrophages and 45 mM for NK, T and B cells.

Chromatin Immobilization: After sonication, chromatin extracts were transferred to a 96 well plate and diluted 1 to 5 with Sonication Equilibration Buffer (10 mM TrisCl, 140 mM NaCl, 0.1% Sodium Deoxycholate, 1% Tx-100, 1 mM EDTA, 1× Protease Inhibitors (Roche) to achieve an SDS concentration of 0.1%. To immobilize the chromatin on magnetic beads, 15 μl of Dynabeads Protein (Life Tech) and 1.3 μg of anti-H3 antibody (ab1791) were added to the diluted chromatin extracts and incubated for 20 hours at 4° C.

Chromatin Indexing: Magnet based bead capture was used to efficiently add, wash and remove the different master mixes used in the indexing process. All the reactions were done while chromatin was bound to the H3 coated magnetic beads. After the immobilization, IP bead bound chromatin immunocomplexes were magnetized and washed 3 times with 150 μl of 10 mM Tris Cl+1× Protease Inhibitors EDTA free (Roche). After the washes bead bound chromatin was re-suspended in 20 ul of the same buffer. Chromatin End Repair was performed by adding 30 µl of a master mix: 25 µl 2× ER mix (50 mM Tris-Cl ph 7.5, 20 mM MgCl₂, 20 mM DTT, 2 mM ATP, 1 mM dNTPs), 2 µl T4 PNK enzyme (10 U/ul NEB), and 2 µl T4 polymerase (3 U/ul NEB) to each well. Samples were incubated in a thermal cycler at 12° C. for 25 min, 25° C. for 25 mM, and finally cooled to 4° C. After end repair, bead bound chromatin was washed once with 150 µl of 10 mM TrisCl+Protease Inhibitors and re-suspended in 40 ul of the same buffer. Chromatin was A-tailed by adding 20 µl master mix (17 µl A-base add mix, 3 µl Klenow (3'→5' exonuclease, 3 U/ul, NEB) to each well and incubated at 37° C. for 30 mM in a thermal cycler. After end repair bead bound chromatin was washed once with 150 ul of 10 mM TrisCl+Protease Inhibitors and re-suspended in 19 ul of the same buffer. Chromatin was indexed by adding 5 ul of 0.75 µM Y-shaped Indexed Adaptors (containing P5 and P7 sequences) to each well which were ligated to the chromatin's DNA ends by adding 34 µl of AL master mix (29 µl 2× Quick Ligation Buffer and 5 µl Quick DNA ligase (NEB) to each well. Samples were thoroughly mixed and incubated at 25° C. for 40 min in a thermal cycler. Bead bound indexed chromatin was washed once with 150 ul of 10 mM TrisCl+Protease Inhibitors to remove the non ligated adaptors.

Chromatin Release: Denaturing conditions (DTT, high salt and detergent) and heat were used to release the indexed chromatin from the antibody coated magnetic beads. Immediately following the post-Indexing wash, samples were taken out of the magnet, beads were re-suspended in 12.5 µl of 100 mM DTT and incubated for 5 mM at Room Temp. Then, 12.5 µl of Chromatin Release Buffer (500 mM NaCl, 2% SDS, 2% Sodium Deoxycholate, 2× protease Inhibitors) were added to each well, samples were mixed thoroughly and incubated at 37° C. for 30 min. After the release incubation, magnetic beads were again thoroughly re-suspended and pooled together in groups of n samples resulting in a pool volume of 200-250 µl. The pooled indexed chromatin samples were concentrated using a 50 KDa cutoff Centricon (Amicon).

Chromatin Immunoprecipitation: Target antibody was added and incubated at 4° C. for 3 h, then 50 µl with Protein G Magnetic beads were added and IP was incubated for 1 more hour. For each ChIP, 1.5 µg of anti H3K4me1 (ab8895) and 2.5 µg of anti H3K4me2 (ab32356), anti H3K4me3 (Millipore, 07-473) and anti H3K27ac (ab4729) were used.

TF iChIP: 50 ul of protein G magnetic Dynabeads (Invitrogen) coupled to target antibody were added and incubated 4 h at 4° C. For the coupling, beads were washed once (200 µl) in a binding/blocking buffer (PBS, 0.5% Tween 20, 0.5% BSA), incubated with 10 µg of antibody in binding/blocking buffer for 1 hour at room temperature, and then washed to remove excess antibody. For each ChIP, 10 µg of anti PU.1 (Santa Cruz, sc352-x) was used.

Washes and ChIPed DNA elation: A 96 well magnet was used (Invitrogen) in all further steps. ChIP Buffer was removed and samples were washed 5 times with cold RIPA (200 µl per wash), twice with RIPA buffer supplemented with 500 mM NaCl (200 µl per wash), twice with LiCl buffer (10 mM TE, 250 mM LiCl, 0.5% NP-40, 0.5% DOC), once with TE (10 mM Tris-HCl pH 8.0, 1 mM EDTA), and then eluted in 50 µl of 0.5% SDS, 300 mM NaCl, 5 mM EDTA, 10 mM Tris HCl pH 8.0. The eluate was treated sequentially with 2 µl of RNaseA (Roche, 11119915001) for 30 mM at 37° C., 2.5 µl of Proteinase K (NEB, P8102S) for two hours at 37° C. and 8 hours at 65° C. to revert formaldehyde crosslinking.

ChIPed DNA isolation: SPRI cleanup steps were performed using 96 well plates and magnets. 90 µl SPRI were added to the reverse-crosslinked samples, pipette-mixed 15 times and incubated for 6 minutes. Supernatant were separated from the beads using a 96-well magnet for 5 minutes. Beads were washed on the magnet with 70% ethanol and then air dried for 5 minutes. The DNA was eluted in 23 µl EB buffer (10 mM Tris-HCl pH 8.0) by pipette mixing 25 times.

Library Amplification, QC and Sequencing: The library was completed and amplified through a PCR reaction with 0.5 µM of PCR forward and PCR reverse primers and PCR ready mix (Kapa Biosystems). The forward primer contains the Illumina P5-Read1 sequences and the reverse primer contains the P7-Read2 sequences. The amplified pooled single-cell library was purified with 1×volumes of SPRI beads. Library concentration was measured with a Qubit fluorometer (Life Technologies) and mean molecule size was determined with a 2200 TapeStation instrument (Agilent Technologies). Library quality was further determined by qPCR, measuring the enrichment of ubiquitous active promoters (Actin-B and GAPDH) versus background (Cryaa). Libraries were size selected with 0.6× volumes of SPRI beads removing large DNA fragments (>600 bp). iChIP libraries were sequenced using an Illumina HiSeq 1500.

RNA isolation: A minimum of 5000 cells were sorted in 200 µl of Lysis/Binding Buffer (Life technologies), lysed for 5 mM and frozen at −80° C. Cell lysates were thawed and messenger RNA was captured with 12 µl of Dynabeads oligo(dT) (Life technologies), and washed according to manufacture guidelines. Purified messenger RNA was eluted at 70° C. with 10 µl of 10 mM Tris-Cl pH 7.5 and stored at −80° C.

RNA seq library construction: The MARS-seq protocol (Science 343, 776-779 (2014)) developed for single cell RNA-seq to produce RNA-seq libraries was used for all the hematopoietic populations. In brief, the protocol consists of special designed primers with unique molecular identifiers for accurate molecule counting and a step of linear amplification of the initial mRNA pool, followed by a library construction step. This way, the diversity of the original pool of messenger RNAs is preserved even if the amount of input RNA is low. A minimum of 2 replicate libraries was prepared for each of the different hematopoietic populations. Table 1 summarizes the primers used in the experiments described herein below.

TABLE 1

| PRIMER NAME | SEQUENCE AND MODIFICATIONS |
|---|---|
| Universal Adaptor | 5'-ACACTCTTTCCCTACACGACGCTCTTCCGATC*T-3', where * indicates phosphothioate modification. (SEQ ID NO: 1) |
| Indexed Adaptors | 5'-GATCGGAAGAGCACACGTCTGAACTCCAGTCACXXXXXXATCTCGTATGCCGTCTTCTGTT-3', (SEQ ID NO: 2) where XXXXXX is the barcode for sample multiplexing |

TABLE 1-continued

| PRIMER NAME | SEQUENCE AND MODIFICATIONS |
|---|---|
| Y-Shaped Indexed adaptors | Anneal ssUniversal Adaptor and ssIndexed Adaptors to obtain Y-shaped Indexed Adaptors. |
| PCR-forward | 5'-AATGATACGGCGACCACCGAGATCTACACTCTTTCCCTACACGAC-3' (SEQ ID NO: 3) |
| PCR-Reverse | 5'-CAAGCAGAAGACGGCATACGAGAT-3' (SEQ ID NO: 4) |
| Barcoded RT primer | 5'-CGATTGAGGCCGGTAATACGACTCACTATAGGGGCGACGTGTGCTCTTCCGATCTXXXXXXNNNNTTTTTTTTTTTTTTTTTTTTN-3', where XXXXXX is the cell barcode and NNNN is the RMT (SEQ ID NO: 5) |
| Ligation adapter | 5'-AGATCGGAAGAGCGTCGTGTAG-3', modified with a phosphate group at 5' and a C3 spacer (blocker) at the 3' (SEQ ID NO: 6) |
| Second RT primer | 5'-TCTAGCCTTCTCGCAGCACATC-3' (SEQ ID NO: 7) |
| P5_Rd1 PCR forward | 5'-AATGATACGGCGACCACCGAGATCTACACTCTTTCCCTACACGACGCTCTTCCGATCT-3' (SEQ ID NO: 8) |
| P7_Rd2 PCR reverse | 5'-CAAGCAGAAGACGGCATACGAGATGTGACTGGAGTTCAGACGTGTGCTCTTCCGATCT-3' (SEQ ID NO: 9) |

The RNAseq protocol used for hematopoietic cells is described below:

1. Linear Amplification of the mRNA pool.

4 μl of purified mRNA were placed in 384-well plates. First, to open secondary RNA structures and allow annealing of the RT primer, the 384-well plate was incubated at 72° C. for 3 min and immediately transferred to 384-well Inheco thermal block integrated to Bravo and set at 4° C. Then, 2 ul of an RT reaction mix (10 mM DTT, 4 mM dNTP, 2.5 U/μl Superscript III RT enzyme in 50 mM Tris-HCl (pH 8.3), 75 mM KCl, 3 mM $MgCl_2$) were added into each well of the 384-well plate and the reaction was mixed one time. Tips were replaced and the process repeated to all wells. The 384-well plate was then spun down and moved into a 384 cycler (Eppendorf) for the following incubation: 2 mm at 42° C., 50 min at 50° C., 5 mm at 85° C. Indexed samples with equivalent amount of cDNA were pooled. The pooled cDNA was converted to double-st-randed DNA with a second strand synthesis kit (NEB) in a 20 μl reaction, incubating for 2.5 h at 16° C. The product was purified with 1.4× volumes of SPRI beads, eluted in 8 μl and in-vitro transcribed (with the beads) at 37° C. overnight for linear amplification using the T7 High Yield RNA polymerase IVT kit (NEB). Following IVT, the DNA template was removed with Turbo DNase I (Ambion) 15 min at 37° C. and the amplified RNA (aRNA) purified with 1.2× volumes of SPRI beads.

2. Library Preparation for High-Throughput Sequencing.

The aRNA was chemically fragmented into short molecules (median size ~200 nucleotides) by incubating 3 mm at 70° C. in $Zn^{2+}$ RNA fragmentation solution (Ambion) and purified with two volumes of SPRI beads. The aRNA (5 μl) was preincubated 3 mm at 70° C. with 1 μl of 100 μM ligation adapter; then, 14 μl of a mix containing 9.5% DMSO, 1 mM ATP, 20% PEG8000 and 1 U/μl T4 ligase in 50 mM Tris HCl pH7.5, 10 mM $MgCl_2$ and 1 mM DTT was added. The reaction was incubated at 22° C. for 2 h. The ligated product was reverse transcribed using Affinity Script RT enzyme (Agilent; reaction mix contains Affinity Script RT buffer, 10 mM DTT, 4 mM dNTP, 2.5 U/μl RT enzyme) and a primer complementary to the ligated adapter. The reaction was incubated for 2 mm at 42° C., 45 mm at 50° C. and 5 mm at 85° C. The cDNA was purified with 1.5× volumes of SPRI beads. The library was completed and amplified through a nested PCR reaction with 0.5 μM of P5_Rd1 and P7_Rd2 primers and PCR ready mix (Kapa Biosystems). The forward primer contains the Illumina P5-Read1 sequences and the reverse primer contains the P7-Read2 sequences. The amplified pooled library was purified with 0.7× volumes of SPRI beads to remove primer leftovers. Library concentration was measured with a Qubit fluorometer (Life Technologies) and mean molecule size was determined with a 2200 TapeStation instrument (Agilent). MARS-Seq libraries were sequenced using an Illumina HiSeq 1500.

ATAC-seq: To profile for open chromatin, the Assay for Transposase Accessible Chromatin (ATAC-seq) protocol developed by Buenrostro et al. (Nat. Methods 10, 1213-1218 (2013)) was used with the following changes: different hematopoietic cell populations were sorted in 400 μl of MACS buffer (1×PBS, 0.5% BSA, 2 mM EDTA) and pelleted by centrifugation for 15 min at 500 g and 4° C. using a swing rotor with low acceleration and brake settings. Cell pellets were washed once with 1×PBS and cells were pelleted by centrifugation using the previous settings. Cell pellets were re-suspended in 25 μl of lysis buffer (10 mM Tris-HCl pH 7.4, 10 mM NaCl, 3 mM $MgCl_2$, 0.1% Igepal CA-630) and nuclei were pelleted by centrifugation for 30 min at 500 g, 4° C. using a swing rotor with low acceleration and brake settings. Supernatant was discarded and nuclei were re-suspended in 25 μl reaction buffer containing 2 μl of Tn5 transposase and 12.5 μl of TD buffer (Nextera Sample preparation kit from Illumina) The reaction was incubated at 37° C. for one hour. Then 5 ul of clean up buffer (900 mM NaCl, 300 mM EDTA), 2 μl of 5% SDS and 2 μl of Proteinase K (NEB) were added and incubated for 30 min at 40° C. Tagmentated DNA was isolated using 2×SPRI beads cleanup. For library amplification, two sequential 9-cycle PCR were performed in order to enrich small tagmentated DNA fragments. 2 μl of indexing primers included in the Nextera Index kit and KAPA HiFi HotStart ready mix were used. After the first PCR, the libraries were selected for small fragments (less than 600 bp) using SPRI cleanup. Then a second PCR was performed with the same conditions in order to obtain the final library. DNA concentration was measured with a Qubit fluorometer (Life Technologies) and library sizes were determined using TapeStation (Agilent Technologies). Libraries where sequenced on a Hiseq 1500 for an average of 20 million reads per sample.

Ex vivo differentiation of BMDCs: To obtain BMDCs, bone marrow cells were plated at a density of 200,000 cells/ml on non-tissue culture treated plastic dishes (10 ml medium per plate). At day 2, cells were fed with another 10 ml medium per dish. At day 5, cells were harvested from 15 ml of the supernatant by spinning at 1400 rpm for 5 minutes; pellets were resuspended with 5 ml medium and added back to the original dish. Cells were fed with another 5 ml medium at day 7. BMDC medium contains: RPMI (Gibco) supplemented with 10% heat inactivated FBS (Gibco), β-mercaptoethanol (50 uM, Gibco), L-glutamine (2 mM, Biological Industries) penicillin/streptomycin (100 U/ml, Biological Industries), MEM non-essential amino acids (1×, Biological Industries), HEPES (10 mM, Biological Industries), sodium pyruvate (1 mM, Biological Industries), and GM-CSF (20 ng/ml; Peprotech).

Harvesting of BMDCs for iChIP titration: Cells were fixed for 8 min with 1% formaldehyde, quenched with glycine and washed twice with ice-cold PBS. Cells were re-suspended in iChIP Harvesting Buffer, counted and transferred to 0.2 ml tubes in 10 ul aliquots containing 10.000, 3.000, 1.000 and 500 cells.

Isolation of hematopoietic progenitor cells: Femora, pelvis and tibiae were extracted from 6 C57BL/6J female mice (8 to 12 weeks old) and bone marrow cells were flushed with MACS buffer. The cells were enriched with CD117/c-kit Microbeads according to the manufacturer's guidelines (AutoMACS, Miltenyi Biotec; order number: 130-091-224). C-kit enriched cells were stained with Lin (Ter119, Gr1, CD11b, B220, CD3, CD4, CD8), c-kit, Sca1, CD34, FcgR-II, Flk2 and IL7R antibodies (eBioscience) for 30 mm and sorted with FACSAria III cell sorter (BD Biosciences). Table 2 herein below summarizes the antibodies used for this experiment.

TABLE 2

| Marker | Fluorophore | Clone | |
|---|---|---|---|
| B220 | e450 | RA3-6B2 | eBioscience |
| B220 | PE | RA-6B2 | eBioscience |
| c-kit | APC | 2B8 | eBioscience |
| CD115 | PE | AFS98 | eBioscience |
| CD11b | e450 | M1/70 | eBioscience |
| CD11b | APC | M1/70 | eBioscience |
| CD19 | PE-Cy7 | Bio1D3 | eBioscience |
| CD3 | e450 | 17A2 | eBioscience |
| CD34 | FITC | RAM34 | eBioscience |
| CD4 | e450 | GK1.5 | eBioscience |
| CD4 | Alexa700 | GK1.5 | eBioscience |
| CD71 | APC | R17217 | eBioscience |
| CD8 | FITC | 53-6.7 | eBioscience |
| CD8a | e450 | 53-6.7 | eBioscience |
| F4/80 | FITC | BM8 | eBioscience |
| FcgR-II | PE-Cy7 | 93 | eBioscience |
| Flk2 | PE | A2F10 | eBioscience |
| Gr1 | e450 | RB6-8C5 | eBioscience |
| Gr1 | PerCP-Cy5.5 | RB6-8C5 | Biolegend |
| I-Ab | PacBlue | AF6-120.1 | eBioscience |
| IL7-R | FITC | A7R34 | eBioscience |
| NK1.1 | e450 | PK136 | eBioscience |
| NK1.1 | APC | PK136 | eBioscience |
| Sca-1 | PerCP-Cy5.5 | D7 | eBioscience |
| TCR-β | FITC | H57-597 | eBioscience |
| Ter119 | e450 | TER-119 | eBioscience |

The cell populations were identified as:
LT-HSC: Lin−, c-Kit+, Sca-1+, Flk2−, CD34−
ST-HSC: Lin−, c-Kit+, Sca-1+, Flk2−, CD34+
MPP: Lin−, c-Kit+, Sca-1+, Flk2+, CD34+
CMP: Lin−, c-Kit+, Sca-1+, FcgRII low, CD34+
GMP: Lin−, c-Kit+, Sca-1+, FcgRII high, CD34+
MEP: Lin−, c-Kit+, Sca-1+, FcgRII−, CD34−
CLPs: Lin−, Flk2+, Il7R+

Isolation of bone marrow derived mature cells: Bone marrow cells were flushed from femora and tibiae of C57BL/6J female mice (8 to 12 weeks old), suspended with MACS buffer and incubated 3 mm in red blood cell lysis solution (Sigma). Cells were stained with CD3, B220, NK1.1, Gr1, CD11b, CD115, F4/80 antibodies (eBioscience), and after filtration through a 70-μm strainer sorted with a FACSAria III cell sorter (BD Biosciences). Table 2 herein above summarizes the antibodies used for this experiment. The cell populations were identified as:
Granulocytes: CD3−, B220−, Nk1.1−, CD11b+, Gr1+, High SSC
Macrophages: CD3−, B220−, F4/80+, CD115−, Low SSC
Monocytes: CD3−, B220−, NK1.1−, F4/80−, CD115+ Low SSC Isolation of splenic lymphoid cells: Spleens were extracted from C57BL/6J female mice (8 to 12 weeks old), dissociated with a gentle MACS Dissociator (Miltenyi Biotec, Germany) into single suspension, and—after washing with MACS buffer—incubated for 5 mm in red blood cell lysis solution (Sigma). Cells were then washed, resuspended in MACS buffer and stained with: CD3, CD4, CD8, B220, CD19, TCR-β, I-Ab, Ter119 and NK1.1 (eBioscience). After washing, cells were filtrated through a 70-μm strainer and sorted with a FACSAria III cell sorter (BD Biosciences). Table 2 herein above summarizes the antibodies used for this experiment. The cell populations were identified as:
B cells: CD3−, B220+, CD19+.
T CD4+ cells: CD3+, B220−, CD4+, CD8−.
T CD8+ cells: CD3+, B220−, CD4−, CD8+.
NK Cells: CD4−, CD8−, B220−, I-Ab−, Ter119−, NK1.1+.

Isolation of splenic erythroid cells: Spleens were extracted from C57BL/6J female mice (8 to 12 weeks old), dissociated into single splenocytes in MACS buffer, with a gentle MACS Dissociator (Miltenyi Biotec, Germany) and stained with: B220, Ter119 and CD71 (eBioscience). After washing, cells were filtrated through a 70-μm strainer and sorted with a FACSAria III cell sorter (BD Biosciences). Table 2, herein above summarizes the antibodies used for this experiment. The cell populations were identified as:
EryA: Ter119+, CD71+, high FSC.
EryB: Ter119+, CD71+, low FSC.

ChIP sequencing and peak finding: ChIP sequencing was done on Illumina HiSeq-1500 and pooled libraries were sequenced at a sequencing depth of ~10-15 million aligned reads per sample. Libraries were prepared in triplicates or duplicates. Reads were mapped to the mouse mm9 assembly using the 'bowtie2' program with the default parameters, only tags that uniquely mapped to the genome were used for further analysis. Due to the initial low cell number per sample (~10,000) and to avoid clonal artifacts introduced in the PCR amplification step, the number of identical reads at each genomic position was restricted to be at most 3.

The identification of ChIP-seq enriched regions (peaks) in each sample was performed using HOMER. For histone modifications, peaks were identified by searching locations of high read density using a 1000 bp sliding window. The present inventors required adjacent peaks to be at least 1000 bp away to avoid redundant detection. The threshold for the number of tags that determined a valid peak was selected at a false discovery rate of 0.001. The following HOMER command was used: cmd=findPeaks <sample tag directory>-L 0-C 3-size 1000-minDist 1000-tbp 3-o <output file>

Construction of enhancer catalog: Peaks from all samples (16 cell types with 2-3 replicates) were combined into one unified catalog for each modification separately. Peaks that did not overlap between at least two replicates (distance between centers>500 bp) were discarded; appearance in one cell type was enough to be included in the final catalog. Redundancy of overlapping peaks (distance between centers<500 bp) was removed by selecting a representative peak as the one with the strongest signal, extended by 1000 bp in each direction from its center. Scatter plots and correlations between replicates were calculated on the vector of log-transformed reads counts for the collection of peaks (FIG. 1D).

In total, the catalog of H3K4me1 and H3K4me2 had 110,844 and 69,970 peaks, respectively, with 66,338 common peaks. To generate the final enhancer catalog, we first counted the number of H3K4me3 reads in each putative peak. A bi-modal distribution of H3K4me3 levels was observed and a 2-Gaussian mixture model was fitted to select a threshold. Regions with high H3K4me3 levels were removed: resulting in 48,415 regions in the final set of enhancers.

From this point onward, this catalog of enhancers was used for the rest of the analysis in this work. For each enhancer in this catalog, the number of reads was counted within 2 kb around its center for each modification. The script annotatePeaks.pl from HOMER package was used, normalizing each library to 10,000,000 reads.

Clustering and correlation analysis: The enhancer catalog was clustered based on H3K4me1 log-transformed counts using K-means (matlab R2012b k means implementation) with K=9. The present inventors have tested other k (5-20) and observed that increasing the number of clusters leads to quantitative refinements of the patterns, but does not introduce new patterns of enhancer change. Correlation matrices for histone modifications between cell types were calculated on the log transformed enhancers catalog.

Enhancer dynamics and state: To define the number of dynamic enhancers, we first divided enhancers into 3 categories for each cell type: 'off' (number of reads<25), 'on' (number of reads>50), and 'intermediate' otherwise Enhancers that were categorized at least once in both 'on' and 'off' state were classified as dynamic. To quantify the number of enhancers that are opened or closed during the differentiation process, we counted the number of 'off'/'on' enhancers at the root of the hematopoietic tree (LT-HSC) that flipped state in the relevant mature cell type. To further determine the precise stage of gain/loss (FIG. 3D), the present inventors examined the path from HSC to mature cells and selected the stage in which the maximal change in H3K4me1 levels occurred.

Enhancer activity was determined based on the ratio of H3K4me1 and H3K27ac levels. The present inventors focused only on the 'on' regions based on H3K4me1 when defining the 'active'/'poised' enhancers. As opposed to the bi-modal distribution observed in H3K4me1 levels over the set of regions, H3K27ac showed a normal distribution. Therefore, they selected a threshold for 'active' regions of H3K27ac reads>25. Changing the threshold influenced the 'active'/'poised' ratio but did not change the relative order of cell types. For example, erythrocytes utilize more enhancers than CMP regardless of the specific threshold selected.

Analysis of ATAC-seq: ATAC-seq data was mapped and analyzed using the same pipeline as ChIP-seq data. A read coverage profile was extracted for each region in the enhancers catalog. The chromatin accessibility value for each enhancer in a given cell type was defined based on the maximum coverage in the region. The catalog was next re-centered based on the position of the maximum value in the ATAC coverage profile.

Motif enrichment analysis: Motifs were searched on 1000 bp window centered on the ATAC center using homer2 command from the HOMER package. For each region, the present inventors extracted the best motif score ('homer2 find –mscore') for each motif in the JASPAR CORE motif catalog (downloaded on March 2014). Enrichment scores were calculated using two-sample Kolmogorov-Smirnov test, comparing the motif scores in the set of 'off' enhancers with those in the 'on' enhancers for each cell type. Motifs corresponding to TFs not expressed in a certain cell type were excluded from the analysis.

Logistic model: To predict enhancer state ('on' or 'off') from its sequence, a logistic model was trained.

First, the present inventors estimated whether each transcription factor was expressed in each cell type. RNA-seq measurements were used, defining "expressed" as having more than 5 reads per million tags, and higher than 20% of its maximal expression levels across all cells.

The training labels were the state of each enhancer in each cell type, removing ones in intermediate state. The predictor was given the scores of the 216 motifs of the enhancer masked by the expression status of the corresponding transcription factor. Thus, the prediction could utilize the motif scores of factors that are expressed in the relevant cell type. Parameters were estimated using matlab R2012b glmfit function. To evaluate accuracy, sensitivity and precision of the model we used 5-fold cross-validation, each time training on 80% of the enhancers X cell types and testing on the remaining 20%. The reported results are the average on 1000 cross validation runs, each with a random partition to 5 folds.

Results

To profile chromatin dynamics of scarce in vivo cell populations, an indexing-first chromatin IP approach (iChIP) was developed. In this protocol, barcoding is performed directly on the total cellular chromatin (FIG. 1A), thereby avoiding the low input enzymatic reactions occurring in conventional ChIP. Importantly, this enables multiple chromatin-barcoded samples to be pooled for ChIP in the same well, further reducing initial input requirements and increasing cross-sample reproducibility. To minimize centrifugation steps, cells are crosslinked before sorting, and sonication. Then, the sheared chromatin is immobilized on anti-H3 antibody-coated magnetic beads and indexed. The indexed chromatin is released from the H3-beads and pooled with chromatin from other samples. Finally, ChIP is performed with the desired antibody, and a single chromatin-barcoded pool can be split to multiple ChIPs for profiling various chromatin modifications.

The iChIP protocol is highly reproducible for low cell numbers (a few hundred cells) while increasing the sensitivity and throughput (FIGS. 1A-D). To benchmark iChIP, decreasing amounts (10,000 to 500 cells) of chromatin isolated from bone-marrow-derived dendritic cells (BM-DCs) were barcoded, in triplicate, and ChIP was performed on the barcoded chromatin with an antibody for mono and tri-methylated histone H3 lysine 4 (H3K4me1 and H3K4me3) (FIGS. 1B-D). Reproducibility of H3K4me3 peaks was confirmed between replicates of 10,000 cells (r=0.95) down to 500 cells (r=0.85). iChIP profiles correlated with conventional ChIP-seq on 10 million BMDCs (r=0.92) (16). iChIP is applicable to profile other histone modifications and transcription factors for low cell numbers (FIGS. 1C-D). The reproducibility and sensitivity for small cell numbers of iChIP open the way for in vivo characterization of chromatin dynamics during hematopoiesis.

Four histone modifications (H3K4me1, H3K4me2, H3K4me3 and H3K27ac) were profiled in three in vivo replicates at 16 developmental stages of hematopoietic commitment using 5,000 cells per mark. The cell populations chosen comprise all multipotent progenitor stages and the common lineage oligopotent progenitors from each of the major blood lineages (myeloid, lymphoid and erythroid) as well as several terminally differentiated cell types from each of the lineages (16). Replicates of histone mark ChIP and RNAseq displayed high reproducibility (average r=0.950). Histone marks were used to define promoter (high H3K4me3) and enhancer (high H3K4me1/2 and low H3K4me3) regions resulting in analysis of 48,415 enhancers and 17,923 promoters Enhancer activity was defined from H3K27ac levels and RNA expression values of the nearest gene (16-18). Genome-wide analysis of RNA expression and promoter activity (H3K4me3 signal) identified four major patterns for progenitors, lymphoid, myeloid and erythroid cells (FIG. 2B). In contrast, H3K4me1 signal revealed that lineage-progenitors were more similar to the differentiated cells within their lineage than to progenitors from other cell lineages (FIG. 2B). This distinction suggests that enhancer establishment is initiated in early lineage commitment and can reveal the differentiation potential of progeny prior to the execution of the RNA expression program.

Changes in chromatin marks during hematopoiesis (particularly H3K4me1 and H3K4me2) suggest lineage specific activity of regulatory elements. Of the 48,415 hematopoietic enhancers, 90% (43,428) changed state during hematopoiesis. It was found that 60% (26,393) of these dynamic enhancers show the stereotypical behavior in which they are initially marked in hematopoietic stem cells (HSCs), but are maintained only in the relevant lineage (FIG. 2C (Gata2)). Surprisingly, it was discovered that a significant proportion of dynamic enhancers (40%, 17,035) are established de novo during the differentiation process (16). For example, enhancers present in myeloid gene loci IL-1b, CD14, S100a8 and F7 (coagulation factor VII) are either established de novo or become more prominent in the myeloid lineage (FIG. 2C). Similarly, Ebf1 and Cr2 enhancers are established in B cells; Bcl11b and CD3 g enhancers in T cells; Granzyme A and Ncr1 enhancers in NK cells; and Gata1, Gypa (Glycophorin A) and Cpox (Coproporphyrinogen Oxidase) enhancers in the erythroid lineage (FIGS. 2A-D).

The establishment of de novo lineage specific enhancers occurs mainly at the root of the commitment point in the first progenitor of the lineage, whereas closing of enhancers occurs more gradually (FIGS. 2A-D). For example, S100a8 and F7-F10 loci display H3K4me1 signal specifically in the myeloid lineage with de novo establishment of the enhancers at the root of the myeloid commitment point in common myeloid progenitor (CMP) (FIG. 2C). Similarly, the Cpox and Gypa loci display H3K4me1 signal specifically in the erythrocyte lineage with de novo establishment of the enhancers at the root of the erythrocyte commitment point in the megakaryocyte erythroid progenitor (MEP) (FIG. 2C). Importantly, a step-wise acquisition of the different chromatin modifications in the lineage-specific enhancers during hematopoiesis was observed (FIG. 2D). For example, in both S100a8 (myeloid lineage) and Gypa (erythroid lineage) loci, H3K4me1/2 appear first in the root lineage progenitor (CMP and MEP, respectively), while H3K27ac (locus activation) is acquired together with active RNA transcription only once the cells (granulocytes and erythrocyte B) are terminally differentiated (FIG. 2D). Globally, 32% of the activated (H3K27ac) enhancers in terminally differentiated cells are initially poised (H3Kme1 only) in the lineage progenitors.

Figures 3A, 3B:
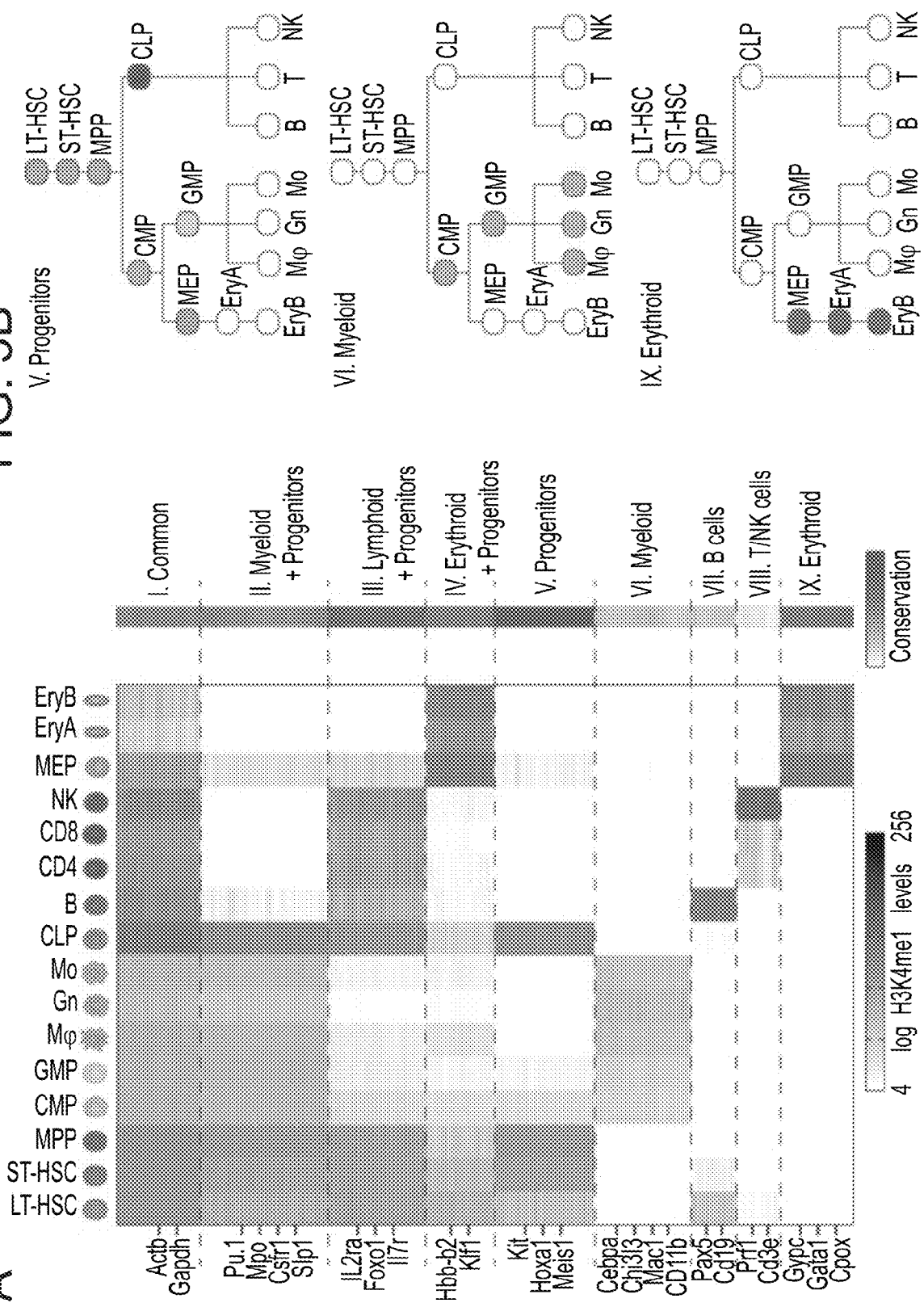

Clustering of all 48,415 H3K4me1 peaks by their dynamic profiles during hematopoiesis revealed nine major clusters, consistent with the underlying biology of the system (FIG. 3A). H3K4me2 signal shows similar patterns in all nine clusters. Cluster I comprises enhancers shared throughout hematopoiesis. Clusters II-IV group lineage-specific enhancers already marked in HSCs and shared with hematopoietic progenitors. Finally, clusters VI (FIG. 3B middle), VII VIII, IX (FIG. 3B bottom) group de novo enhancers that are specific to a particular lineage and were not marked in HSCs; with 6382 myeloid, 5834 lymphoid and 4819 erythroid enhancers. A group of 6612 enhancers (Cluster V) was also found which shared exclusively among progenitors (FIG. 3B top). Interestingly, the erythrocyte and progenitor enhancer clusters exhibit relatively high sequence conservation in the mammalian clade, with the myeloid and lymphoid enhancers displaying lower conservation. These data suggests differential rates of evolutionary dynamics in these cis regulatory regions (FIG. 3A).

Newly formed enhancers could either be established at a specific branching point or established gradually during the development process. To further examine these dynamics, the present inventors generated a catalog of enhancers that are dynamic (gained or lost) during the process of differentiation from the long-term hematopoietic stem cells (LT-HSCs) to mature, terminally differentiated cells (FIG. 3C). It was determined, for each enhancer, the stage of gain/loss along the differentiation path. In erythroid differentiation 65% of the de novo enhancer repertoire are gained in the MEP stage (FIG. 3D). Similarly, 40-50% of the de novo myeloid enhancers are gained in the first step of myeloid commitment, during the multipotent progenitor (MPP) to CMP transition, while the CMP to GMP transition involves fewer gains (15-30%). Together, the CMP and GMP stages are responsible for 63-80% of gained enhancers in terminally differentiated myeloid cells (FIG. 3D), consistent with the global enhancer similarity of CMP and GMP with the myeloid lineage (FIG. 2B). In contrast, enhancer loss is a more gradual process that initiates in the CMP or MEP stage (for myeloid and erythrocyte development, respectively) with a large proportion (40-50%) of enhancers lost in the last and definitive differentiation step to mature cells.

Genome wide studies show that, while H3K4me1 marks both poised and active enhancers, H3K27ac marks only active enhancers (19, 20). Since poised enhancers represent potential gene expression programs, the ratio of these enhancers in a given cell type approximates the current regulatory potential of the cell (20). Analysis of the regulatory potential in hematopoiesis shows that progenitor cells are more plastic than differentiated cell types, with erythrocytes utilizing most (78%) of their enhancers, whereas CMPs use only 33% of their enhancer potential (FIG. 3E-F). Within the progenitor group, CMP and GMP are more plastic than the multipotent stem cells (33-37% versus 62-65% of enhancer use); likely due to the de novo expansion of myeloid enhancers (FIGS. 2B, 3A and F). Notably there is a wide spectrum of plasticity across the terminally differentiated cells, with the myeloid lineage (macrophages, monocytes and granulocytes) showing higher degrees of plasticity than erythrocytes, B, and NK cells; this is consistent with the higher functional versatility of myeloid cells in comparison to other hematopoietic cell types (21).

De novo H3K4me1 establishment in hematopoiesis is concomitant to increase in chromatin accessibility (FIG. 4A, B). Chromatin accessibility, 'open chromatin' (22) was measured, during the developmental process in ten hematopoietic cell types using the assay for transposase-accessible chromatin followed by sequencing (ATAC-seq) (23). In erythroid (Gypa) and myeloid (F7 and F10) gene loci chromatin accessibility follows the temporal pattern observed for H3K4me1 (FIG. 4A). As expected, ATAC signal is enriched both in active promoters and H3K4me1-positive enhancers, as well as in insulators and other regulatory regions (23). To evaluate the proportion of de novo enhancers that also display de novo establishment of open chromatin, the present inventors plotted the ATAC-seq signal in the regions from the H3K4me1 enhancer catalog. They compared the ATAC-seq signal to H3K4me1 and H3K27ac intensities. We observed a similar pattern between ATAC and H3K4me1 signal (r=0.75) and a weakened agreement with H3K27ac (r=0.62) (FIG. 4B) suggesting that the process of gain or loss of H3K4me1 mark on enhancers occurs concomitantly with formation of open chromatin sites.

Figure 4D:
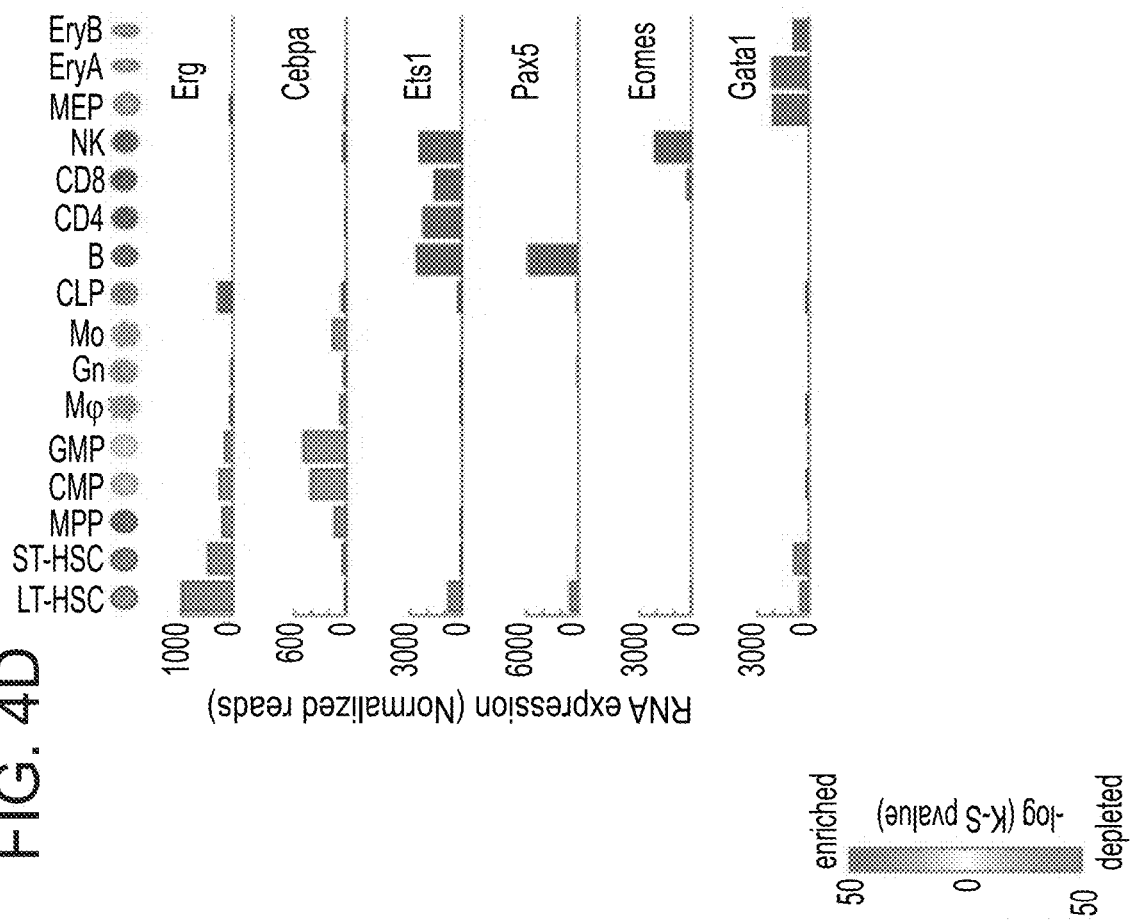
Figure 4C:
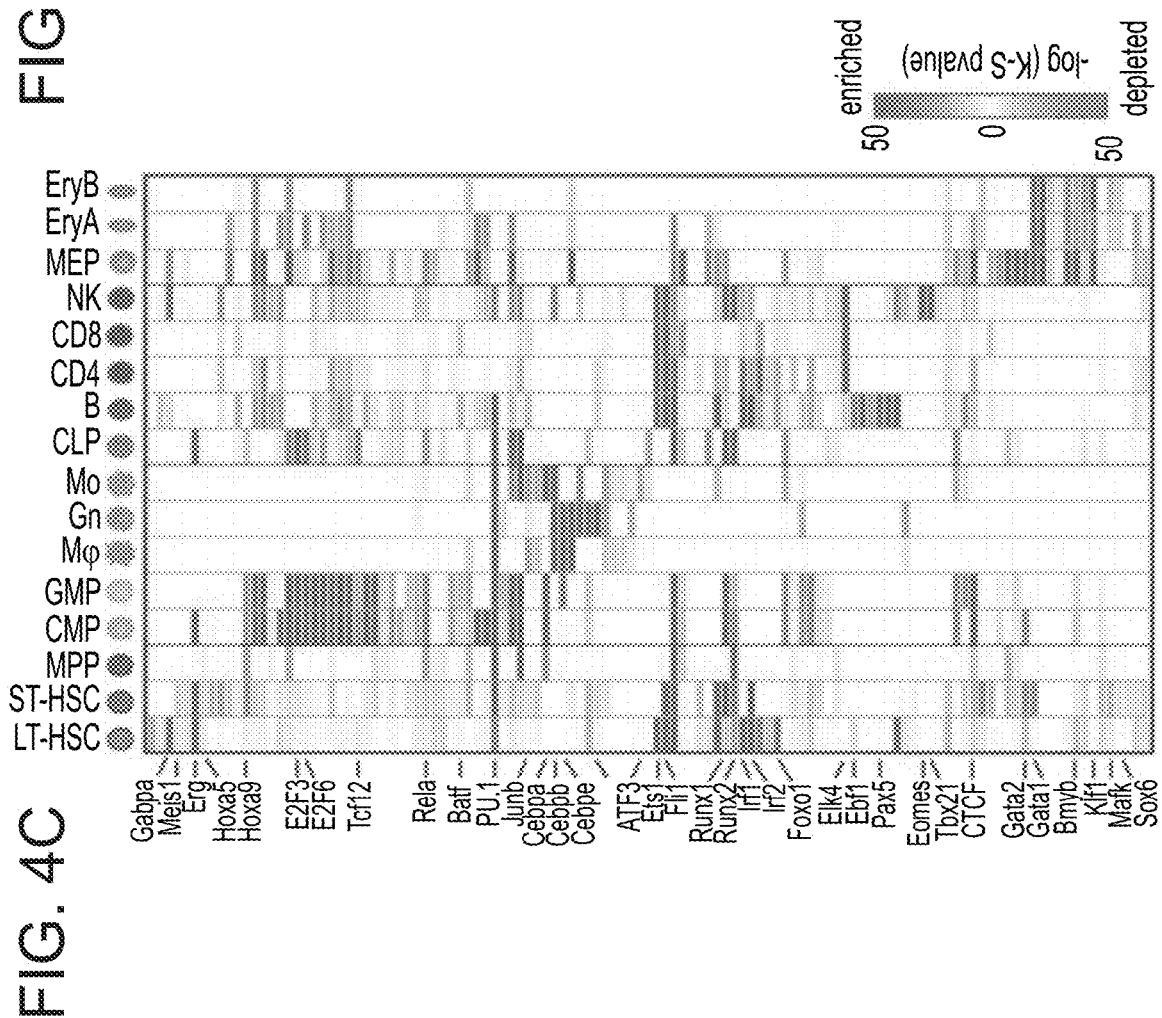
Figures 4E, 4F:
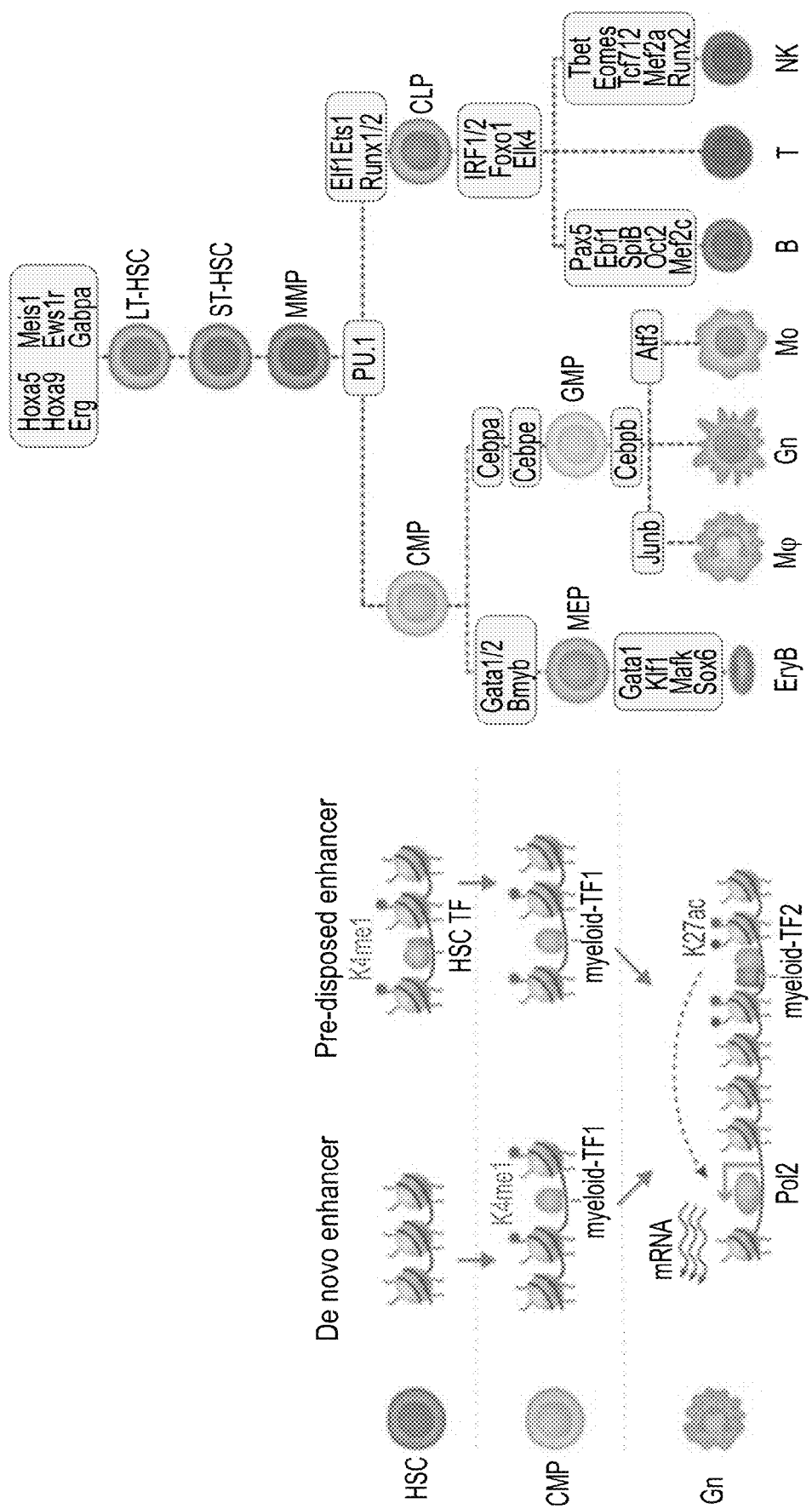

Establishment of lineage specific enhancers is regulated by the activity of lineage specific transcription factors (24) (FIG. 4C-E). Using the ATAC peaks (16) and the enhancer catalog described herein, they searched for enriched transcription factor binding motifs in each cell type (FIG. 4C) in order to identify lineage-determining factors. It was found that, in line with their identified functions, PU.1, Gata1, and Foxo1 can be classified as potential regulators of myeloid, erythroid and lymphoid enhancers, respectively (3, 11, 25, 26).

To systematically identify potential regulators, the present inventors generated a logistic regression model to predict enhancer activity at each stage from the DNA binding motif scores and TF expression (FIG. 4D, E). The logistic model accurately predicts enhancer cell-type specific activity with 75% accuracy (with 70% sensitivity and 80% specificity). Importantly, the model allowed them to elucidate the transcription factors controlling chromatin dynamics and lineage specification in hematopoiesis (25, 26). The model identified the known myeloid lineage determining factors, PU.1, Cebpb and Cebpa as regulators of myeloid enhancers; additionally, the model suggests a hierarchy between the Cebp factors with Cebpa active in the progenitors (CMP/GMP) and Cebpb replacing Cebpa in the differentiated cell types (FIG. 4E). Similarly, Meis1, Hoxa9 and Erg were identified as potential regulators of stem cell enhancers, Pax5 in B cells, Klf1 in erythroid cells and Ets1 in lymphoid cells (FIGS. 4C-E). Many transcription factors that have been implicated in lineage development but have not previously been associated with chromatin regulation of lineage determination were identified like Irf1 and Irf2 in B cells and Cebpe in granulocytes (27, 28). New potential regulators of hematopoietic lineages are highlighted: ATF3 in monocytes and Tcf712, Mef2a and Runx2 in NK cells (FIG. 4E). All together, the present findings show that chromatin is highly dynamic during hematopoiesis, orchestrated by a defined set of transcription factors.

In conclusion, iChIP enables the execution of reproducible and sensitive ChIP on only a few hundred cells in a manner broadly applicable across organisms and tissues. It was shown that poised enhancers are established in lineage progenitors before their activation and precede RNA expression in subsequent lineage differentiation. These enhancers are established concomitantly with the formation of open chromatin sites. The present inventors then showed that most of enhancer dynamics can be accounted for by the activity of known lineage-specific factors as well as new candidate regulators. These results suggest a new model for chromatin dynamics during differentiation (FIG. 4F) and show that development involves massive dynamic reorganization of the chromatin landscape. While some enhancers are preset in hematopoietic stem cells, as suggested by the conventional development model, a comparable number of enhancers appear to be established de novo during hematopoiesis. It may be surmised that the establishment of newly poised enhancers in the early lineage commitment steps initiates regulatory programs that are subsequently applied in differentiated cells, while closing of enhancers occurs during later differentiation stages. This suggests that cellular enhancer potential reaches its maximum not at the HSC stage, but during the oligopotent progenitor stages. Taken together, these observations reshape the present understanding of the role of chromatin and pioneer factors during differentiation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of analyzing DNA which, in a cell, is bound to a DNA binding moiety, the method comprising:

(a) obtaining at least two samples of complexes of DNA bound to a DNA binding moiety, wherein said DNA is derived from a cell sample comprising 100-10,000 cells;

(b) crosslinking said DNA to said DNA binding moiety;
(c) isolating said complexes on a solid support;
(d) labeling the DNA of said complexes, wherein said labeling distinguishes between said complexes of the first of said at least two samples and said complexes of the second of said at least two samples;
(e) pooling said at least two samples of complexes; and
(f) isolating said complexes using an agent which specifically binds to said DNA binding moiety; and
(g) analyzing said DNA of said complexes.

2. The method of claim 1, wherein said labeling is effected using a tagment DNA enzyme.

3. The method of claim 1, wherein step (c) is effected using an antibody attached to said solid support.

4. The method of claim 1, wherein said analyzing comprises sequencing said DNA.

5. The method of claim 1, further comprising amplifying said DNA following step (f) and prior to step (g).

6. The method of claim 1, further comprising analyzing said DNA binding moiety of said complex.

7. The method of claim 1, wherein said first sample is derived from a first cell type and said second sample is derived from a second cell type.

8. The method of claim 1, wherein said labeling is effected at the 5' and the 3' end of said DNA.

9. The method of claim 1, wherein said labeling comprises a DNA barcode.

10. The method of claim 1, further comprising sonicating said DNA following step (b) and prior to step (c) such that said DNA is no longer than 500 bases.

11. The method of claim 1, wherein said DNA binding moiety is a DNA binding protein.

12. The method of claim 11, wherein said DNA binding protein is a histone.

13. The method of claim 1, wherein said agent is an antibody.

14. The method of claim 1, not being carried out using a microfluidic device.

* * * * *

SEQUENCE LISTING

```
<160> NUMBER OF SEQ ID NOS: 10

<210> SEQ ID NO 1
<211> LENGTH: 33
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
```

-continued

```
<222> LOCATION: (32)..(32)
<223> OTHER INFORMATION: phosphothionate modification

<400> SEQUENCE: 1
acactctttc cctacacgac gctcttccga tct                               33

<210> SEQ ID NO 2
<211> LENGTH: 61
<212> TYPE: DNA
<213> ORGANISM: Artificial Sequence
<220> FEATURE:
<223> OTHER INFORMATION: Single strand DNA oligonucleotide
<220> FEATURE:
<221> NAME/KEY: misc_feature
<222> LOCATION: (34)..(39)
<223> OTHER INFORMATION: barcode for sample multiplexing
<220> FEATURE:
<221> NAME/KEY: misc_feature
<222> LOCATION: (34)..(39)
<223> OTHER INFORMATION: a or g or c or t/u, unknown, or other

<400> SEQUENCE: 2
gatcggaaga gcacacgtct gaactccagt cacnnnnnna tctcgtatgc cgtcttctgt    60
t                                                                    61

<210> SEQ ID NO 3
<211> LENGTH: 45
<212> TYPE: DNA
<213> ORGANISM: Artificial Sequence
<220> FEATURE:
<223> OTHER INFORMATION: Single strand DNA oligonucleotide

<400> SEQUENCE: 3
aatgatacgg cgaccaccga gatctacact ctttccctac acgac                    45

<210> SEQ ID NO 4
<211> LENGTH: 24
<212> TYPE: DNA
<213> ORGANISM: Artificial Sequence
<220> FEATURE:
<223> OTHER INFORMATION: Single strand DNA oligonucleotide

<400> SEQUENCE: 4
caagcagaag acggcatacg agat                                           24

<210> SEQ ID NO 5
<211> LENGTH: 86
<212> TYPE: DNA
<213> ORGANISM: Artificial Sequence
<220> FEATURE:
<223> OTHER INFORMATION: Barcoded RT Single strand DNA oligonucleotide
      primer
<220> FEATURE:
<221> NAME/KEY: misc_feature
<222> LOCATION: (56)..(65)
<223> OTHER INFORMATION: a or g or c or t/u, unknown, or other
<220> FEATURE:
<221> NAME/KEY: misc_feature
<222> LOCATION: (56)..(61)
<223> OTHER INFORMATION: barcode for sample multiplexing
<220> FEATURE:
<221> NAME/KEY: misc_feature
<222> LOCATION: (62)..(65)
<223> OTHER INFORMATION: RMT
<220> FEATURE:
<221> NAME/KEY: misc_feature
<222> LOCATION: (86)..(86)
<223> OTHER INFORMATION: a or g or c or t/u, unknown, or other

<400> SEQUENCE: 5
```

-continued

```
cgattgaggc cggtaatacg actcactata ggggcgacgt gtgctcttcc gatctnnnnn    60
nnnnnttttt tttttttttt tttttn                                        86

<210> SEQ ID NO 6
<211> LENGTH: 22
<212> TYPE: DNA
<213> ORGANISM: Artificial Sequence
<220> FEATURE:
<223> OTHER INFORMATION: Single strand DNA oligonucleotide Ligation
      adapter
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (22)..(22)
<223> OTHER INFORMATION: 3' C3 spacer (blocker)

<400> SEQUENCE: 6
agatcggaag agcgtcgtgt ag                                            22

<210> SEQ ID NO 7
<211> LENGTH: 22
<212> TYPE: DNA
<213> ORGANISM: Artificial Sequence
<220> FEATURE:
<223> OTHER INFORMATION: Single strand DNA oligonucleotide

<400> SEQUENCE: 7
tctagccttc tcgcagcaca tc                                            22

<210> SEQ ID NO 8
<211> LENGTH: 58
<212> TYPE: DNA
<213> ORGANISM: Artificial Sequence
<220> FEATURE:
<223> OTHER INFORMATION: Single strand DNA oligonucleotide

<400> SEQUENCE: 8
aatgatacgg cgaccaccga gatctacact ctttccctac acgacgctct tccgatct    58

<210> SEQ ID NO 9
<211> LENGTH: 58
<212> TYPE: DNA
<213> ORGANISM: Artificial Sequence
<220> FEATURE:
<223> OTHER INFORMATION: Single strand DNA oligonucleotide

<400> SEQUENCE: 9
caagcagaag acggcatacg agatgtgact ggagttcaga cgtgtgctct tccgatct    58

<210> SEQ ID NO 10
<211> LENGTH: 35
<212> TYPE: DNA
<213> ORGANISM: Artificial Sequence
<220> FEATURE:
<223> OTHER INFORMATION: T7 RNA polymerase promoter sequence

<400> SEQUENCE: 10
cgattgaggc cggtaatacg actcactata ggggc                              35
```